US005695959A

United States Patent [19]
Jackson et al.

[11] Patent Number: 5,695,959
[45] Date of Patent: Dec. 9, 1997

[54] RECOMBINANT EXPRESSION OF INSECTICIDALLY EFFECTIVE SPIDER TOXIN

[75] Inventors: John Randolph Hunter Jackson; Karen Joanne Krapcho; Janice Helen Johnson, all of Salt Lake City; Robert Marden Kral, Jr., Midvale, all of Utah

[73] Assignees: FMC Corporation, Philadelphia, Pa.; NPS Pharmaceuticals, Inc., Salt Lake City, Utah

[21] Appl. No.: 457,272

[22] Filed: Jun. 1, 1995

Related U.S. Application Data

[62] Division of Ser. No. 89,998, Jul. 7, 1993, Pat. No. 5,457,178.

[51] Int. Cl.[6] .......... C12P 21/02; C12N 15/63; C12N 1/21; A61K 31/715

[52] U.S. Cl. .......... 435/69.1; 435/320.1; 435/252.3; 435/325; 435/348; 514/44

[58] Field of Search .......... 435/320.1, 252.3, 435/240.1, 69.1, 325, 348; 514/44

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,703,008 | 10/1987 | Lin | 435/240.2 |
| 4,797,279 | 1/1989 | Karamata et al. | 424/93 |
| 4,855,405 | 8/1989 | Yoshioka et al. | 530/300 |
| 4,861,595 | 8/1989 | Barnes et al. | 424/195.1 |
| 4,879,236 | 11/1989 | Smith et al. | 435/235 |
| 4,918,107 | 4/1990 | Nakajima et al. | 514/616 |
| 4,925,664 | 5/1990 | Jackson et al. | 424/537 |

FOREIGN PATENT DOCUMENTS

| | | |
|---|---|---|
| 2005658 | 6/1990 | Canada . |
| 0 325 400 A1 | 7/1989 | European Pat. Off. . |
| 0 340 948 | 11/1989 | European Pat. Off. . |
| 0 374 940 | 6/1990 | European Pat. Off. . |
| 0 395 357 | 10/1990 | European Pat. Off. . |
| 0 431 829 | 6/1991 | European Pat. Off. . |
| 0 505 207 | 9/1992 | European Pat. Off. . |
| WO 89/07608 | 8/1989 | WIPO . |
| WO 92/16637 | 10/1992 | WIPO . |
| WO 93/23428 | 11/1993 | WIPO . |

OTHER PUBLICATIONS

Adams, et al., "Isolation and Biological Activity of Synaptic Toxins from the Venom of The Funnel Web Spider, *Agelenopsis aperta*", in Insect Neurochemistry and Neuro-physiology 1986, Borkevec and Gelman, eds., Humana Press, New Jersey, 1986.

Carbonell, et al., "Synthesis of a gene coding for an insect-specific scorpion neurotoxin and attempts to express it using baculovirus vectors", *Gene*, 73:409–418 (1988).

Chomczynski, et al., "Single-Step Method of RNA Isolation by Acid Guanidinium Thiocyanate-Phenol-Chloroform Extraction", *Analytical Biochemistry*, 162:156–159 (1987).

Cutler, et al., "Electroporation: Being Developed to Transform Crops, (success with model crop confirmed)", *AG Biotech. News*, 7(5):3 & 17 (1990).

Davies, et al., "Recombinant baculovirus vectors expressing gluthathione-S-transferase fusion proteins", *Biotech.*, 11:933–936 (1993).

Dunwiddie, T.V., "The Use of In Vitro Brain Slices in Neuropharmacology", *Electrophysiological Techniques in Pharmacology*, H.M. Geller, 25ed. Alan R. Liss, Inc., New York, pp. 65–90 (1986).

Fuqua, et al., "A simple PCR Method for detection and cloning low abundant transcript", *Biotechniques*, 9:206–211 (1990).

Hink, et al., "Expression of three recombinant proteins using baculovirus vectors in 23 insect cell lines", *Biotechnol. Prog.*, 7:9–14 (1991).

Jackson and Parks, "Spider Toxins: Recent Applications in Neurobiology", *Ann Rev Neurosci.*, 12:405–414 (1989).

Jones, et al., "Molecular Cloning Regulation and Complete Sequence of a Hemocyanin-Related Juenile Hormone-Suppressible Protein From Insect Hemolymphs", *J. Biol. Chem.*, 265:8596 (1990).

Miller, et al., "Bacterial, Viral and Fungal Insecticides", *Science*, 219:715–721 (1983).

Rossi, et al., "An Alternate Method for Synthesis of Double-Stranded DNA Segments", *J. Biol. Chem.*, 257:9226 (1982).

Saiki, et al., "Primer-Directed Enzymatic Amplification of DNA with a Thermostable DNA Polymerase", *Science*, 239:487–491, 1988.

Scopes, "Measurement of Protein by Spectrophotometry at 205 nm", *Anal. Biochem.*, 59:277–282, 1974.

Skinner, et al., "Purification and characterization of two classes of neurotoxins from the funnel web spider, *Agelenopsis aperta*", *J. Biol. Chem.*, 264:2150–2155 (1989).

Stapleton, et al., "Curtatoxins, neurotoxic insecticidal polypeptides isolated from the funnel web spider *Hololena curta*", *J. Biol. Chem.* 265:2054–2059 (1990).

Stewart, et al., "Construction of an improved baculovirus insecticide containing an insect-specific toxic gene", *Nature*, 352:85–88 (1991).

Summers and Smith, "A Manual of Methods for Baculovirus Vectors and Insect Cell Culture Procedures", *Texas Agricultural Experiment Bulletin*, No. 1555, 1, 1988.

(List continued on next page.)

*Primary Examiner*—Robert A. Wax
*Assistant Examiner*—Kowai Lau
*Attorney, Agent, or Firm*—Woodcock Washburn Kurtz Mackiewicz & Norris, LLP

[57] ABSTRACT

This invention provides a family of insecticidally effective proteins and particular members of that family which may be isolated from the venom of the spider *Filistata hibernalis*, DNA encoding such proteins, insecticidal compositions of these proteins or the DNA encoding them, and methods for controlling invertebrate pests. Recombinant expression vectors and host cells and methods for producing insecticidally effective peptides are also provided.

19 Claims, 12 Drawing Sheets

OTHER PUBLICATIONS

Tomalski and Miller, "Insect paralysis by baculoirus-mediated expression of a mite neurotoxic gene", *Nature*, 352:82–85 (1991).

Vialard, et al., "Synthesis of the Membrance Fusion and Hemagglutinin Proteins of Measles Virus, Using a Novel Baculovirus Vector Containing the β–Galactosidase Gene", *J. Virology*, 64:37–50 (1990).

Waddel and Hill, "A Simple Ultraviolet Spectrophotometric Method for the Determination of Protein", *J. Lab. Clin. Med.* 48:311–314 (1956).

Zlotkin, et al., "An Excitatory and a Depressant Insect Toxin from Scorpion Venom both Affect Sodium Conductance and Possess a Common Binding Site", *Arch. Biochem. and Biophysics*, 240:877–887 (1985).

McCutchen, et al., "Development of a Recombinant Baculovirus Expressing an Insect–Selective Neurotoxin: Potential for Pest Control", *Biotechnology*, 9:848–852, 1991.

Bentzien, "Biology of the Spider *Diguetia imperiosa*", *The Pan–Pacific Entomologist*, 49:110–123, 1973.

Quicke, et al., "Extended summaries Pesticides Group and Physicochemical and Biophysical Panel Symposium Novel Approaches in Agrochemical Research", *Pestic. Sci.*, 20:315–317, 1987.

Quistad, et al., "Insecticidal Activity of Spider (Araneae), Centipede (Chilopoda), Scorpion (Scorpionida), and Snake (Serpentes) Venoms", *J. Econ. Entom.*, 85:33–39, 1992.

Nentwig, et al. "Comparative Investigations on the Effect of the Venoms of 18 Spider Species onto the Cockroach *Blatta orientalis* (Blattodea)", *Zool. Jb. Physiol.* 96:279–290 (1992).

Friedel, et al., "Immobilizing and Lethal Effects of Spider Venoms on the Cockroach and the Common Mealbeetle", *Toxicon*, 27:305–316, 1989.

Roth, "The Spider Genus Tegenaria in the Western Hemisphere (Agelenidae)", *Amer. Museum Novitates*, 2323:1–33, 1968.

Vest, "Necrotic Arachnidism in the Northwest United States and Its Probably Relationship to *Tegenaria Agrestis* (Walckenaer) Spiders", *Toxicon*, 25:175–184, 1987.

Creighton, "Modification of the Amino and Carboxyl Terminal Groups", *Proteins: Structure and Molecular Properties*, W.H. Freeman and Company: New York, pp. 75–76, 1983.

Blobel, "Intracellular Protein Topogenesis", *Proc. Natl. Acad. Sci. USA*, 77:1496–1500, 1980.

Raineri, et al., "Agrobacterium–Mediated Transformation of Rice (Oryza Sativa L.)", *Biotechnology*, 8:33–38, 1990.

Fromm, et al., "Inheritance and Expression of Chimeric Genes in the Progeny of Transgenic Maize Plants", *Biotechnology*, 8:833–839, 1990.

Smith, et al. "$M_r$ 26,000 antigen of *Schistosoma japonicum* recognized by resistant WEHI 129/J mice is a parasite gluthathione S–transferase", *Proc. Natl. Acad. Sci. USA*, 83:8703–8707, 1986.

Raymond, "Presentation d'un programme Basic d'analyse log–probit pour micro–ordinateur", *Set. Ent. med et Parasitol.*, 23:117–121 1985.

Luria, et al., *In General Virology*, John Wiley and Sons: New York, Chapter 2, pp. 21–32, 1978.

Kuroda, et al., "Synthesis of Biologically Active Influenza Virus Hemagglutinin in Insect Larvae", *J. of Virology*, 63:1677–1685, 1989.

Wood, "Protease Degradation of *Autographa californica* Nuclear Polyhedrosis Virus Proteins", *Virology*, 103:392–399, 1980.

Price, et al., "Complementation of recombinant baculoviruses by coinfection with wild–type facilitates production in insect larvau of antigenic proteins of hepatitis B virus and influenza virus", *Proc. Natl. Acad. Sci. USA*, 86:1453–1456, 1989.

Bers, et al., "Protein and Nucleic Acid Blotting and Immunobiochemical Detection", *BioTechniques*, 3:276–288, 1985.

Bronstein, et al., "Rapid and Sensitive Detection of DNA in Southern with Chemiluminescence", *BioTechniques*, 8:310–314, 1990.

Quistad, et al., "Paralytic and Insecticidal Toxins from the Funnel Web Spider, *Hololena curta*", *Toxicon*, 29:329–336, 1991.

Bowers, et al., "Identification and purification of an irreversible presynaptic neurotoxin from the venom of spider *Hololena curta*", *Proc. Natl. Acad. Sci. USA*, 84:3506–3510, 1987.

Geren, "Neurotoxins and Necrotoxins of Spider Venoms", *J. Toxicol.–Toxin Reviews*, 5:161–170, 1986.

Grishin, "Toxic components from *Buthus eupeus* and *Lycosa singoriensis* venoms", in Front. Bioorg. Chem. Mol. Biol., Proc. Int. Symp. (1980), Ananchenko, S.N. Ed., (Oxford, Eng, Pergammon), pp. 93–96.

Hermann and Frischauf, "Isolation of Genomic DNA", *Methods in Enzymology*, 152:180–183, 1987.

Kaneda, et al., "Scorpion toxin prolongs an inactivation phase of the voltage–dependent sodium current in rat isolated single hippocampal neurons", *Brain Res.*, 487:192–195, 1989.

McKnight, et al., "Transcriptional Control Signals of an Eucaryotic Protein–Coding Gene", *Science*, 217:316, 1982.

TBW Assay Results

| Sample | Dose (µg/g) | TBW paralysis 24 hr |
|---|---|---|
| Metal 1 | 22.7 | 3 slight N/F |
| Metal 2 | 19.9 | 3/5 |
| Metal 3 | 21.0 | 0/5 |
| Controls | 0 | 0/5 |

NF = not feeding
Controls were injected with 10 µl of PBS, pH 6.5.

TBW Assay Results

| Sample | Dose (μg/g) | TBW paralysis 24 hr |
|---|---|---|
| AX 1* | 20 | 2/3 |
| AX 2* | 20 | 3/3 |
| AX 3 | 19 | 3/3 |
| AX 4 | 22 | 1/3, 1 partial |
| AX 5 | 22 | 0/3, 1 FI |
| Controls | 0 | 0/5 |

FI = feeding inhibition
Controls were injected with 10 μl of PBS, pH 6.5.

*AX 1 and AX 2 fractions tested were from a previous, equivalent chromatography.

TBW Assay Results

| Sample | Dose (μg/g) | TBW paralysis 24 hr |
|---|---|---|
| Metal 1 | 19.2 | 1/3 |
| Metal 2 | 20.9 | 3/3 |
| Metal 5 | >20 | 2/3 |
| Controls | 0 | 0/5 |

Controls were injected with 10 μl of PBS, pH 6.5.

TBW Assay Results

| Sample | Dose (μg/g) | TBW paralysis 24 hr |
|---|---|---|
| AX 1 | 19.7 | 2/3 |
| AX 2 | 22.7 | 2/3 |
| AX 3 | 20.5 | 2/3, 1 partial |
| AX 4 | 20.8 | 2/3, 1 N/F |
| AX 5 | 18.2 | 1/3 |
| Controls | 0 | 0/5 |

N/F = not feeding.
Controls were injected with 10 μl of PBS, pH 6.5.

TBW Assay Results

| Sample | Dose (µg/g) | TBW paralysis 24 hr |
|---|---|---|
| AX 1 | 19.7 | 2/3 |
| AX 2 | 22.7 | 2/3 |
| AX 3 | 20.5 | 2/3, 1 partial |
| AX 4 | 20.8 | 2/3, 1 N/F |
| AX 5 | 18.2 | 1/3 |
| Controls | 0 | 0/5 |

N/F = not feeding.
Controls were injected with 10 µl of PBS, pH 6.5.

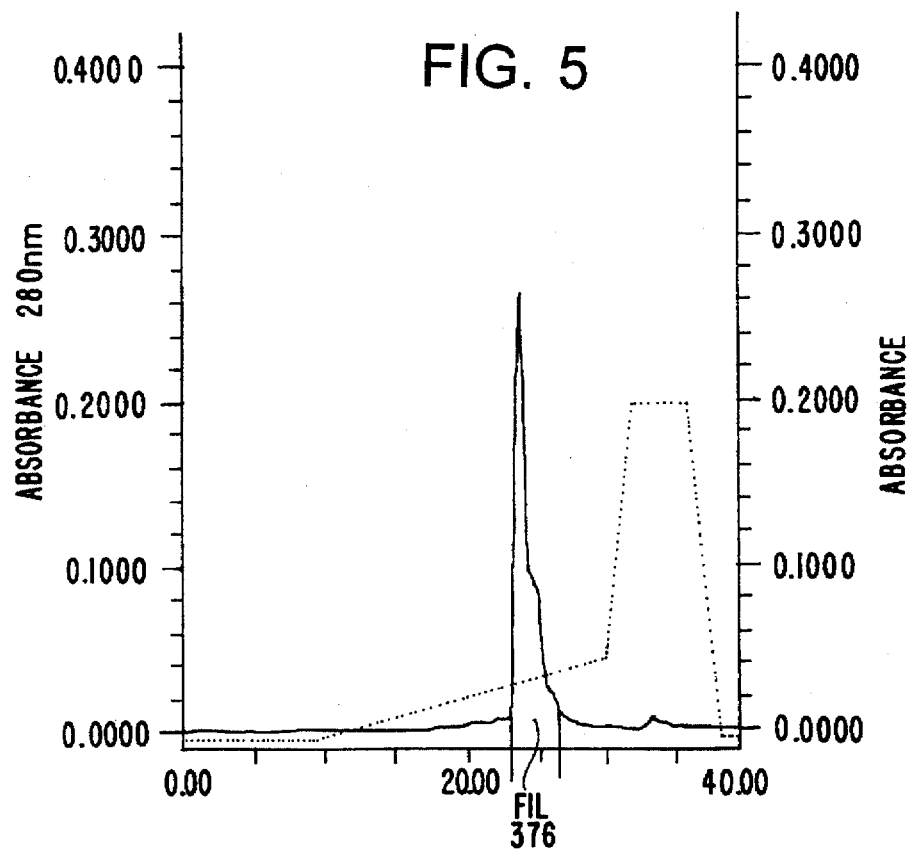
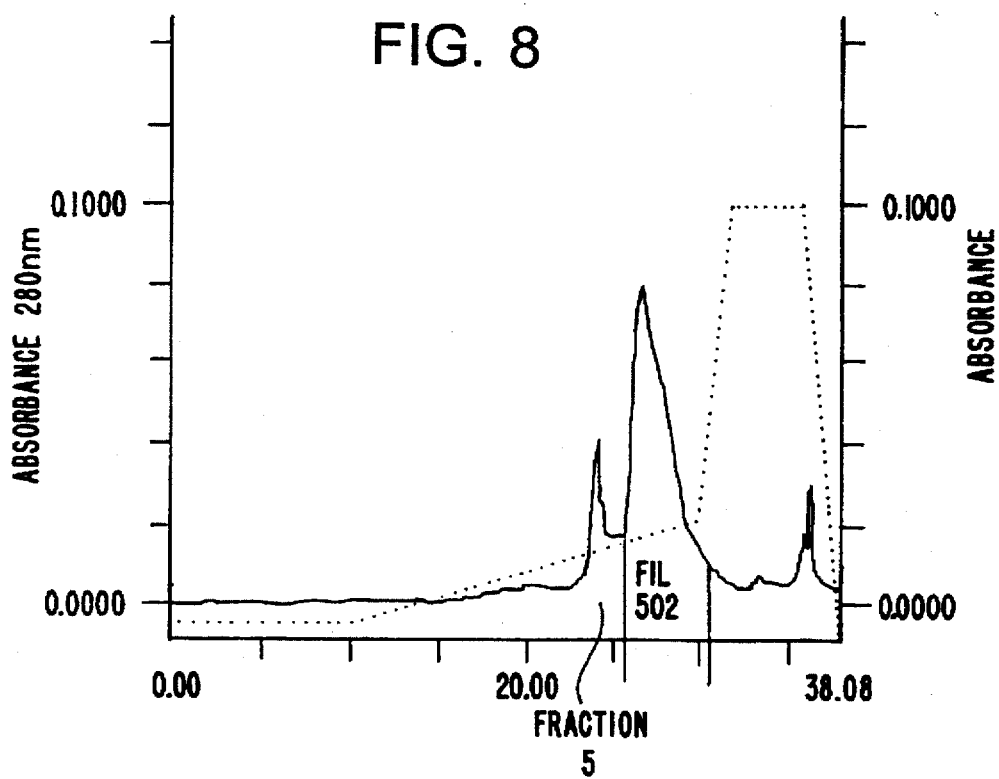

TBW Assay Results

| Sample | Dose (μg/g) | TBW paralysis 24 hr |
|---|---|---|
| Fraction 2 | <10 | 0/3 |
| FIL-376 | 18.3 | 3/3 |
| Controls | 0 | 0/5 |

Controls were injected with 10 μl of PBS, pH 6.5.

TBW Assay Results

| Sample | Dose (μg/g) | TBW paralysis 24 hr |
|---|---|---|
| FIL-377 | 20.8 | 2/3 |
| Controls | 0 | 0/5 |

Controls were injected with 10 μl of PBS, pH 6.5.

TBW Assay Results

| Sample | Dose (μg/g) | TBW paralysis 24 hr |
|---|---|---|
| FIL-502 | 17.0 | 2/5, 1 N/F |
| Controls | 0 | 0/5 |

N/F = not feeding.
Controls were injected with 10 μl of PBS, pH 6.5.

TBW Assay Results

| Sample | Dose (µg/g) | TBW paralysis 24 hr |
|---|---|---|
| AX 1 | 25 | 2/3, 1 N/F |
| AX 2 | 18.1 | 2/3, 1 slight |
| AX 3 | 19.2 | 0/3 |
| Controls | 0 | 0/5 |

N/F = not feeding.
Controls were injected with 10 µl of PBS, pH 6.5.

TBW Assay Results

| Sample | Dose (μg/g) | TBW paralysis 24 hr |
|---|---|---|
| HIC 1 | 7.6 | 0/3 |
| FIL-501 | 12.7 | 1/3 |
| HIC 3 | 9.7 | 0/3 |
| Controls | 0 | 0/5 |

Controls were injected with 10 μl of PBS, pH 6.5.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 940 base pairs
( B ) TYPE: nucleic acid
( C ) STRANDEDNESS: double
( D ) TOPOLOGY: unknown ( x i ) SEQUENCE DESCRIPTION: SEQ ID NO:1:

| NNN | NNN | NNN | NNN | NNG | TTG | TAC | ATG | GAA | ATT | GTT | GTT | ATC | TGT | 42 |
|---|---|---|---|---|---|---|---|---|---|---|---|---|---|---|
| Xaa | Xaa | Xaa | Xaa | Xaa | Leu | Tyr | Met | Glu | Ile | Val | Val | Ile | Cys | |
| 1 | | | | 5 | | | | | 10 | | | | | |

| GAC | AAC | AAC | ATG | TTT | AAG | AAA | TAC | AAA | GGA | GAC | GTA | ACA | TTT | 84 |
|---|---|---|---|---|---|---|---|---|---|---|---|---|---|---|
| Asp | Asn | Asn | Met | Phe | Lys | Lys | Tyr | Lys | Gly | Asp | Val | Thr | Phe | |
| 15 | | | | | 20 | | | | 25 | | | | | |

| ATA | AAG | GAC | AGA | GTC | GGT | GCT | ATA | ATA | AAC | GGT | GCA | AGT | GCA | 126 |
|---|---|---|---|---|---|---|---|---|---|---|---|---|---|---|
| Ile | Lys | Asp | Arg | Val | Gly | Ala | Ile | Ile | Asn | Gly | Ala | Ser | Ala | |
| | 30 | | | | | 35 | | | | | 40 | | | |

| CTT | CTT | TCT | CTA | GTA | AAC | ATT | TTC | CCC | ACC | TTG | CAA | ACT | ACC | 168 |
|---|---|---|---|---|---|---|---|---|---|---|---|---|---|---|
| Leu | Leu | Ser | Leu | Val | Asn | Ile | Phe | Pro | Thr | Leu | Gln | Thr | Thr | |
| | | 45 | | | | | 50 | | | | | 55 | | |

| CGT | ATA | TGG | ATG | CTG | GAA | GAT | AGA | TTT | GAA | GTG | ACT | ACA | AGT | 210 |
|---|---|---|---|---|---|---|---|---|---|---|---|---|---|---|
| Arg | Ile | Trp | Met | Leu | Glu | Asp | Arg | Phe | Glu | Val | Thr | Thr | Ser | |
| | | | 60 | | | | | 65 | | | | | 70 | |

| GCT | ATG | GAT | ACT | CTA | AAC | AAT | TTT | ATA | AAG | TTT | AGA | ACA | GAA | 252 |
|---|---|---|---|---|---|---|---|---|---|---|---|---|---|---|
| Ala | Met | Asp | Thr | Leu | Asn | Asn | Phe | Ile | Lys | Phe | Arg | Thr | Glu | |
| | | | | 75 | | | | | 80 | | | | | |

| TCT | TTA | TTG | AAA | CAC | GAA | CCA | CAT | GAC | AAC | GCA | GTT | CTC | ATA | 294 |
|---|---|---|---|---|---|---|---|---|---|---|---|---|---|---|
| Ser | Leu | Leu | Lys | His | Glu | Pro | His | Asp | Asn | Ala | Val | Leu | Ile | |
| 85 | | | | | 90 | | | | | 95 | | | | |

| GCG | GGT | GAA | AAA | TAT | GAT | CAC | GGG | GTC | GCT | GGT | AAT | GCT | TAT | 336 |
|---|---|---|---|---|---|---|---|---|---|---|---|---|---|---|
| Ala | Gly | Glu | Lys | Tyr | Asp | His | Gly | Val | Ala | Gly | Asn | Ala | Tyr | |
| | 100 | | | | | 105 | | | | | 110 | | | |

| GTG | GGT | GCC | ATA | TGT | GGA | GAC | AGC | TCC | GCT | GAA | AAT | GTT | GTG | 378 |
|---|---|---|---|---|---|---|---|---|---|---|---|---|---|---|
| Val | Gly | Ala | Ile | Cys | Gly | Asp | Ser | Ser | Ala | Glu | Asn | Val | Val | |
| | | 115 | | | | | 120 | | | | | 125 | | |

| GAC | TAC | AGT | GAC | GTC | ATA | GGC | TTA | GTC | GGT | TCA | AAC | ACT | GCT | 420 |
|---|---|---|---|---|---|---|---|---|---|---|---|---|---|---|
| Asp | Tyr | Ser | Asp | Val | Ile | Gly | Leu | Val | Gly | Ser | Asn | Thr | Ala | |
| | | | 130 | | | | | 135 | | | | | 140 | |

| CAC | GAA | ATG | GGA | CAC | AAT | CTT | GGA | TCA | AAT | CAC | GAT | GAT | GAT | 462 |
|---|---|---|---|---|---|---|---|---|---|---|---|---|---|---|
| His | Glu | Met | Gly | His | Asn | Leu | Gly | Ser | Asn | His | Asp | Asp | Asp | |
| | | | | 145 | | | | | 150 | | | | | |

| GGA | ACA | AAA | TGC | CAA | TGT | GAG | GAT | GAA | ATA | TGT | GTT | ATG | TAC | 504 |
|---|---|---|---|---|---|---|---|---|---|---|---|---|---|---|
| Gly | Thr | Lys | Cys | Gln | Cys | Glu | Asp | Glu | Ile | Cys | Val | Met | Tyr | |
| 155 | | | | | 160 | | | | | 165 | | | | |

| CCT | TTT | ATG | CCC | GAG | TCT | CCC | CCA | AAG | CAT | TGG | TCT | TCA | TGT | 546 |
|---|---|---|---|---|---|---|---|---|---|---|---|---|---|---|
| Pro | Phe | Met | Pro | Glu | Ser | Pro | Pro | Lys | His | Trp | Ser | Ser | Cys | |
| | 170 | | | | | 175 | | | | | 180 | | | |

| TCC | AAG | AAA | GCT | TTT | GAT | GAT | GCC | AGA | GCC | AGT | GAT | AAA | TAT | 588 |
|---|---|---|---|---|---|---|---|---|---|---|---|---|---|---|
| Ser | Lys | Lys | Ala | Phe | Asp | Asp | Ala | Arg | Ala | Ser | Asp | Lys | Tyr | |
| | | 185 | | | | | 190 | | | | | 195 | | |

| AGC | TGC | TTA | AAA | AAT | AGA | CCC | ATG | AAA | CTT | AGT | TCA | TCA | ACC | 630 |
|---|---|---|---|---|---|---|---|---|---|---|---|---|---|---|
| Ser | Cys | Leu | Lys | Asn | Arg | Pro | Met | Lys | Leu | Ser | Ser | Ser | Thr | |
| | | | 200 | | | | | 205 | | | | | 210 | |

| TGT | GGT | AAT | GGG | AAA | TTA | GAA | GAG | GGC | GAA | GAA | TGT | GAT | TGT | 672 |
|---|---|---|---|---|---|---|---|---|---|---|---|---|---|---|
| Cys | Gly | Asn | Gly | Lys | Leu | Glu | Glu | Gly | Glu | Glu | Cys | Asp | Cys | |

```
                             215                         220
GGT  GAC  GAA  GAT  ACT  TGT  GAC  GAC  GAA  TGC  TGT  GAT  GCA  ACG      714
Gly  Asp  Glu  Asp  Thr  Cys  Asp  Asp  Glu  Cys  Cys  Asp  Ala  Thr
225                      230                      235

AAT  TGT  CAG  AGA  CTA  AGA  GGC  GAC  CTT  TGC  TCT  TAAGACTTAT         757
Asn  Cys  Gln  Arg  Leu  Arg  Gly  Asp  Leu  Cys  Ser
          240                      245

GTATATTTTC  TTGCCATACG  ACAATAGGTT  AAACTGGAAT  CTACTTCTAC                807

GGCTAAAATG  TATCTTTTGT  CGTTATAGAA  GTTAAAAATG  TAATTACTTA                857

CAACAATTTC  TGTAAACTTG  TGTCTTTCAA  AAAATAAAAG  TTTGGTATGC                907

AATGAAAAAA  AAAAAAAAAA  AAAAAAAAAA  AAA                                   940
```

( 2 ) INFORMATION FOR SEQ ID NO:2:

( i ) SEQUENCE CHARACTERISTICS:
        ( A ) LENGTH: 249 amino acid residues
        ( B ) TYPE: amino acid
        ( D ) TOPOLOGY: unknown ( x i ) SEQUENCE DESCRIPTION: SEQ ID NO:2:

```
Xaa  Xaa  Xaa  Xaa  Xaa  Leu  Tyr  Met  Glu  Ile  Val  Val  Ile  Cys  Asp
1                   5                   10                            15

Asn  Asn  Met  Phe  Lys  Lys  Tyr  Lys  Gly  Asp  Val  Thr  Phe  Ile  Lys
                    20                  25                            30

Asp  Arg  Val  Gly  Ala  Ile  Ile  Asn  Gly  Ala  Ser  Ala  Leu  Leu  Ser
                    35                  40                            45

Leu  Val  Asn  Ile  Phe  Pro  Thr  Leu  Gln  Thr  Thr  Arg  Ile  Trp  Met
                    50                  55                            60

Leu  Glu  Asp  Arg  Phe  Glu  Val  Thr  Thr  Ser  Ala  Met  Asp  Thr  Leu
                    65                  70                            75

Asn  Asn  Phe  Ile  Lys  Phe  Arg  Thr  Glu  Ser  Leu  Leu  Lys  His  Glu
                    80                  85                            90

Pro  His  Asp  Asn  Ala  Val  Leu  Ile  Ala  Gly  Glu  Lys  Tyr  Asp  His
                    95                  100                           105

Gly  Val  Ala  Gly  Asn  Ala  Tyr  Val  Gly  Ala  Ile  Cys  Gly  Asp  Ser
                    110                 115                           120

Ser  Ala  Glu  Asn  Val  Val  Asp  Tyr  Ser  Asp  Val  Ile  Gly  Leu  Val
                    125                 130                           135

Gly  Ser  Asn  Thr  Ala  His  Glu  Met  Gly  His  Asn  Leu  Gly  Ser  Asn
                    140                 145                           150

His  Asp  Asp  Asp  Gly  Thr  Lys  Cys  Gln  Cys  Glu  Asp  Glu  Ile  Cys
                    155                 160                           165

Val  Met  Tyr  Pro  Phe  Met  Pro  Glu  Ser  Pro  Pro  Lys  His  Trp  Ser
                    170                 175                           180

Ser  Cys  Ser  Lys  Lys  Ala  Phe  Asp  Asp  Ala  Arg  Ala  Ser  Asp  Lys
                    185                 190                           195

Tyr  Ser  Cys  Leu  Lys  Asn  Arg  Pro  Met  Lys  Leu  Ser  Ser  Ser  Thr
                    200                 205                           210

Cys  Gly  Asn  Gly  Lys  Leu  Glu  Glu  Gly  Glu  Glu  Cys  Asp  Cys  Gly
                    215                 220                           225

Asp  Glu  Asp  Thr  Cys  Asp  Asp  Glu  Cys  Cys  Asp  Ala  Thr  Asn  Cys
                    230                 235                           240

Gln  Arg  Leu  Arg  Gly  Asp  Leu  Cys  Ser
                    245
```

( 2 ) INFORMATION FOR SEQ ID NO:3:

( i ) SEQUENCE CHARACTERISTICS:
        ( A ) LENGTH: 40 amino acid residues
        ( B ) TYPE: amino acid
        ( D ) TOPOLOGY: unknown ( x i ) SEQUENCE DESCRIPTION: SEQ ID NO:3:

```
Ser  Asn  Asp  Glu  Pro  Leu  Tyr  Met  Glu  Ile  Val  Val  Ile  Xaa  Asp
1                   5                        10                       15

Asn  Asn  Met  Phe  Lys  Lys  Tyr  Lys  Gly  Xaa  Val  Thr  Phe  Ile  Lys
                    20                       25                       30

Asp  Arg  Val  Gly  Ala  Ile  Ile  Asn  Gly  Ala
                    35                       40
```

( 2 ) INFORMATION FOR SEQ ID NO:4:

( i ) SEQUENCE CHARACTERISTICS:
        ( A ) LENGTH: 30 amino acid residues
        ( B ) TYPE: amino acid
        ( D ) TOPOLOGY: unknown ( x i ) SEQUENCE DESCRIPTION: SEQ ID NO:4:

```
Leu  Glu  Asp  Pro  Tyr  Lys  Ser  Asp  Ser  Asn  Ser  Arg  Tyr  Ile  Glu
1                   5                        10                       15

Val  Val  Val  Val  Asn  Asp  Asn  Ser  Met  Phe  Arg  Lys  Tyr  Asn  Arg
                    20                       25                       30
```

( 2 ) INFORMATION FOR SEQ ID NO:5:

( i ) SEQUENCE CHARACTERISTICS:
        ( A ) LENGTH: 40 amino acid residues
        ( B ) TYPE: amino acid
        ( D ) TOPOLOGY: unknown ( x i ) SEQUENCE DESCRIPTION: SEQ ID NO:5:

```
Gly  Gly  Ser  Asp  Pro  Glu  Tyr  Met  Glu  Leu  Val  Val  Ile  Asn  Asp
1                   5                        10                       15

Asn  Lys  Met  Phe  Arg  Lys  Tyr  Gly  Ser  Xaa  Thr  Xaa  Xaa  Val  Ala
                    20                       25                       30

Glu  Xaa  Xaa  Xaa  Gln  Xaa  Met  Asn  Ile  Ala
                    35                       40
```

( 2 ) INFORMATION FOR SEQ ID NO:6:

( i ) SEQUENCE CHARACTERISTICS:
        ( A ) LENGTH: 21 amino acid residues
        ( B ) TYPE: amino acid
        ( D ) TOPOLOGY: unknown ( x i ) SEQUENCE DESCRIPTION: SEQ ID NO:6:

```
Ser  Asp  Glu  Glu  Ser  Val  Xaa  Glu  Thr  Glu  Ile  Xaa  Lys  Glu  Xaa
1                   5                        10                       15

Ala  Ile  Xaa  Leu  Xaa  Asn
                    20
```

RECOMBINANT EXPRESSION OF INSECTICIDALLY EFFECTIVE SPIDER TOXIN

This is a division of application Ser. No. 08/089,998, filed Jul. 7, 1993 now U.S. Pat. No. 5,457,178.

FIELD OF THE INVENTION

This invention relates to insecticidally effective proteins. More particularly, the invention relates, inter alia, to a family of insecticidally effective proteins which may be isolated from Filistata spider venom as well as methods for controlling invertebrate pests.

BACKGROUND OF THE INVENTION

In recent years, scientists and the general public have become increasingly aware that the use of conventional chemical insecticides may have undesirable environmental consequences. These include groundwater contamination, toxicity to non-target organisms such as birds and fish, and potential human health hazards arising from acute or chronic exposure. However, the need for effective insect control has not diminished. This has prompted researchers to develop novel agents for insect control, including improved microbial insecticides.

The most widely used microbial pesticides are derived from the bacterium *Bacillus thuringiensis* (hereinafter B.t.). This bacterial agent is used to control a variety of pests, including leaf-eating caterpillars, beetles and mosquitos. U.S. Pat. No. 4,797,279 issued Jan. 10, 1989 to Karamata et al., discloses hybrid bacterial cells comprising the gene coding for B.t. kurstaki delta-endotoxin and the gene coding for B.t. tenebrionis delta-endotoxin and their preparation. The B.t. hybrids are active against pests susceptible to B.t. kurstaki strains as well as against pests susceptible to B.t. tenebrionis strains. Generally, these hybrids have useful insecticidal properties which are superior to those observed by physical mixtures of the parent strains in terms of level of insecticidal activity, or in terms of spectrum of activity, or both. The insecticidal compositions comprising such microorganisms may be used to combat insects by applying the hybrids in an insecticidally effective amount to the insects or to their environment.

Another derivation from the bacterium B.t. was disclosed in European Patent Application, Publication No. 0 325 400 A1, issued to Gilroy and Wilcox. This invention relates to a hybrid toxin gene which is toxic to lepidopteran insects. Specifically, the invention comprises a hybrid delta endotoxin gene comprising part of the B.t. var. kurstaki HD-73 toxin gene and part of the toxin gene from B.t. var. kurstaki strain HD-1. The hybrid toxin gene (DNA) encoding a protein having activity against lepidopteran insects was disclosed.

The bacterium B.t. was also utilized for its insecticidal properties in European Patent Application, Publication No. 0 340 948, issued to Wilcox, et al. This invention concerns hybrid pesticidal toxins which are produced by the fusion of an insect gut epithelial cell recognition region of a B.t. gene to diphtheria toxin B chain to prepare a hybrid B.t. toxin which is active against lepidopteran insects. It was suggested that the hybrid B.t. gene may be inserted into a plant or cloned into a baculovirus to produce a toxin which can be recovered. Alternatively, the host containing the hybrid B.t. gene can be used as an insecticide by direct application to the environment of the targeted insect.

In the search for insecticidal compounds, scorpion venom was identified as a possible source of compounds providing insecticidal properties. Two insect selective toxins isolated from the venom of the scorpion *Leirus quinquestriatus quinquestriatus* were revealed in Zlotkin, et al., "An Excitatory and a Depressant Insect Toxin from Scorpion Venom both Affect Sodium Conductance and Possess a Common Binding Site," *Arch Biochem and Biophysics*, 240: 877–87 (1985). In a study related to their chemical and pharmacological properties, it was revealed that one toxin induced fast excitatory contractive paralysis of fly larvae and the other induced slow depressant flaccid paralysis. Both affected sodium conductance in neurons.

Canadian Patent 2,005,658 issued Jun. 19, 1990 to Zlotkin, et al., discloses an insecticidally effective protein derived from the scorpion *Leiurus quinquestriatus hebraeus*. In this invention, the venom is lyophilized and separated into fractions. The fraction with the highest toxicity to blowfly larvae and the lowest toxicity to mice was subjected to further purification and the final product is that referred to as "LqhP35".

Corresponding with the research and development related to various compositions having insecticidal properties, researchers worked to develop methods for producing insecticidal genes and introducing these to the target to be protected, or into microbial delivery systems. U.S. Pat. No. 4,879,236 issued Nov. 7, 1989 to Smith and Summers, relates to a method for incorporating a selected gene coupled with a baculovirus promoter into a baculovirus genome to produce a recombinant baculovirus expression vector capable of expression of the selected gene in an insect cell. The method involves cleaving baculovirus DNA to produce a DNA fragment comprising a polyhedrin gene or portion thereof, including a polyhedrin promoter. To prepare a recombinant transfer vector, the DNA fragment is inserted into a cloning vehicle and then a selected gene is inserted into this modified cloning vehicle such that it is under the control of the polyhedrin promoter. The recombinant transfer vector is then contacted in insect cells with a baculovirus DNA so as to effect recombination and incorporation of the selected gene into the baculovirus genome. The baculovirus *Autographa californica* (AcMNPV) and its associated polyhedrin promoter were found to be useful in producing a viral expression vector capable of extremely high levels of expression of a selected gene in an insect host cell.

The inventors suggest that the expression vector might be used in a system for controlling insects by selecting a gene which produces a protein which is toxic to a specific insect or to a spectrum of insects and cloning that gene into the AcMNPV expression vector. They suggest that the vector could be applied to the plant or animal to be protected. The recombinant virus could invade the cells of the intestinal wall following ingestion by the insect and begin replication.

A method for producing insecticidal genes and introducing them to the target to be protected was disclosed in Cutler, "Electroporation Being Developed to Transform Crops: Success with Model Crop Confirmed," AG Biotech. News vol. 7(5):3 & 17 (1990). This article teaches that DNA may be electroporated directly into germinating pollen and that pollen may be put back on the flower to form seeds which then grow into transformed plants. This method has been employed successfully in tobacco plants and may be successful in corn and alfalfa as well. This method may be easier than the electroporation of protoplasts because the ultimate goal is to pollinate the flowers and "let the flowers do the work" rather than to regenerate the plant. The process consists of collecting pollen, germinating it in a germinating medium for 30–60 minutes after which the pollen tube will start to come out of the pollen grain, adding the desired DNA to the liquid suspension containing the pollen, administering an electric shock to open the pores of the pollen, washing the excess DNA away, and putting the altered pollen under the stigma of a plant and waiting until seeds are formed. This may be an easy method to move any gene into crop plants.

An additional delivery system was disclosed in U.S. Pat. No. 4,861,595 issued Aug. 29, 1989 to Barnes and Edwards. This invention concerns the use of treated, substantially intact, microbial cells as a delivery system of protein compounds to animals and humans. The microbial cells initially produce a protein intracellularly via a homologous gene. The protein-producing microbe is treated by chemical or physical means while the cell is substantially intact. Manipulation of the treatment process produces a nonproliferative treated microbial cell without significant loss of the activity of the intracellular compound. Since the cell will not replicate and will have a stable cell wall which may then be broken down in a desired area of the digestive system of the animal or human, it allows the timed or targeted release of the products encapsulatable by the subject invention. After suitable treatment, the protein-producing microbial cell itself is used as the delivery system so no purification of the produced compound is necessary. Any protein, polypeptide, amino acid, or compound, including insecticides, that may be produced by microbial means may be the starting material of the invention.

The possibility of using DNA technology to incorporate a selected toxin with a baculovirus is described in Tomalski et al., "Insect paralysis by baculovirus-mediated expression of a mite neurotoxin gene", Nature, 352: 82–85 (1991) and Stewart et al., "Construction of an improved baculovirus insecticide containing an insect-specific toxin gene", Nature, 352: 85–88 (1991); McCutchen, et al., "Development of a recombinant Baculovirus expressing an insect selective Neurotoxin: Potential for Pest Control," Biotechnology, 9: 848–851 (1991).

Researchers have also been able to isolate toxins extracted from the venom of spiders. U.S. Pat. No. 4,925,664 issued to Jackson and Parks on May 15, 1990, discloses methods of treating heart and neurological diseases by applying toxins derived from the spiders *Agelenopsis aperta* and *Hololena curta*. The toxins are also effective as specific calcium channel or excitatory amino acid receptor blockers that may be used against insects and related pests.

Another study related to the properties of isolated spider venom toxins revealed the ability of low molecular weight factors isolated from funnel-web spider venoms to reversibly bind to calcium channels. WO 89/07608 issued Aug. 24, 1989 to Cherksey, et al., discloses that these active low molecular weight factors reversibly bind to calcium channels with sufficient specificity and affinity to extinguish calcium conductance in neurons and to permit isolation and purification of calcium channel structures. These venoms were found to be toxic to mammals.

Other applications of spider toxins were discussed in Jackson and Parks, "Spider Toxins: Recent Applications in Neurobiology," Ann Rev *Neurosci* 12: 405–14 (1989). This article teaches that there is great heterogeneity in the toxins of different taxa. It recognizes that experiments have suggested species-specific properties of calcium channels and the spider venoms might provide calcium channel antagonists. The spider venoms discussed are found to affect vertebrates. The article also identifies spider venoms as possible sources of insect-specific toxins for agricultural applications.

Adams, et al., "Isolation and Biological Activity of Synaptic Toxins from the Venom of the Funnel Web Spider, *Agelenopsis aperta*," in Insect Neurochemistry and Neurophysiology 1986, Borkovec and Gelman eds., Humana Press, New Jersey, 1986, teaches that multiple peptide toxins which antagonize synaptic transmission in insects have been isolated from the spider *Agelenopsis aperta*.

U.S. Pat. No. 4,855,405 issued Aug. 8, 1989 to Yoshioka et al., discloses a receptor inhibitor obtained from Joro spider (*Nephila clavata*) venom, and its manufacturing method. Yoshioka demonstrates that their toxins show glutamate receptor inhibitory activity in an insect electrophysiological assay.

U.S. Pat. No. 4,918,107 issued Apr. 17, 1990 to Nakajima et al., relates to a compound which has glutamate receptor inhibitor activity, a process for preparing the same, and an insecticidal composition containing the same.

Accordingly, due to a combination of problems associated with conventional chemical insecticides, including pest resistance and injurious effects on non-target organisms, there exists a continuing need for the development of novel means of invertebrate pest control.

SUMMARY OF THE INVENTION

There are provided by this invention novel insecticidally effective proteins derived from, for example, a spider of the genus Filistata. Four insecticidal proteins were isolated from the fractionation of Filistata venom. The proteins are designated FIL-376, FIL-377, FIL-501 and FIL-502. The invention further provides a family of structurally related proteins.

Further provided by this invention are methods for controlling invertebrate pests with insecticidal compositions containing insecticidal proteins or the genes encoding these proteins and insecticidal compositions.

Still further provided by this invention are novel recombinant expression vectors and genetically engineered insecticidal microbes and methods of controlling invertebrate pests comprising contacting said pests with a recombinant baculovirus capable of expressing an effective amount of an insecticidally effective peptide substantially isolatable from Filistata spider venom and agriculturally or horticulturally acceptable salts thereof.

DETAILED DESCRIPTION OF THE DRAWINGS

Figures 1A, 1B:
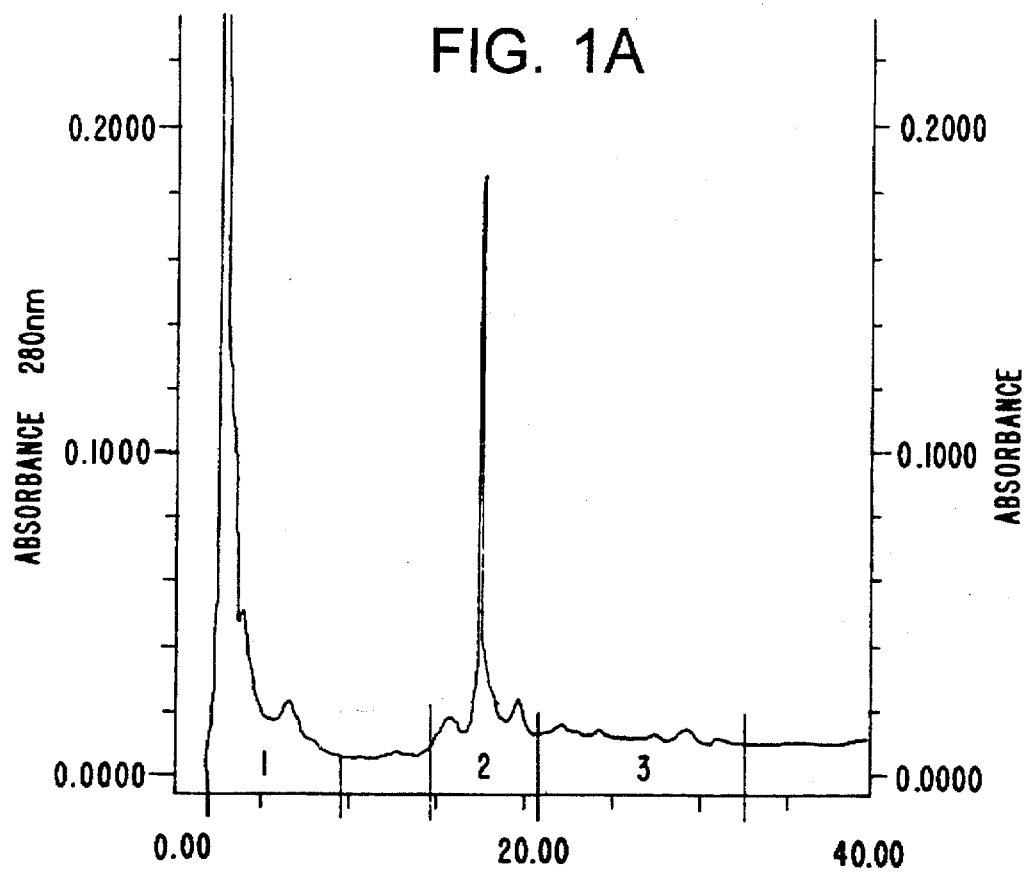

FIG. 1: Chromatography (FIG. 1A) of 8 µl of *Filistata hibernalis* venom by immobilized metal ion affinity chromatography (IMAC) and bioassay (FIG. 1B) of the fractions in tobacco budworm (TBW).

FIG. 2: Anion exchange chromatography (FIG. 2A) of 50 µl of *Filistata hibernalis* venom on the HEMA-IEC BIO Q column and bioassay (FIG. 2B) of the fractions in TBW.

Figures 3A, 3B:
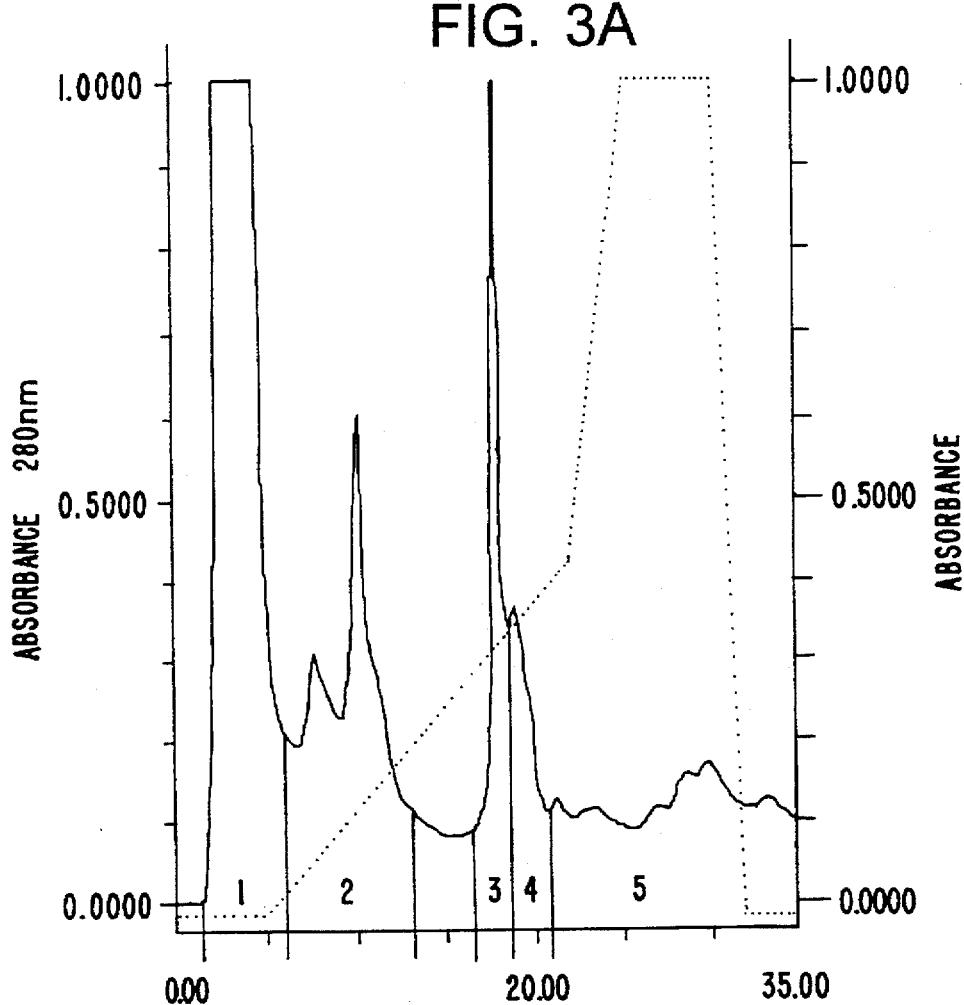

FIG. 3: Chromatography (FIG. 3A) of 400 µl of *Filistata hibernalis* venom by IMAC and bioassay (FIG. 3B) of the fractions in TBW.

Figure 4C:
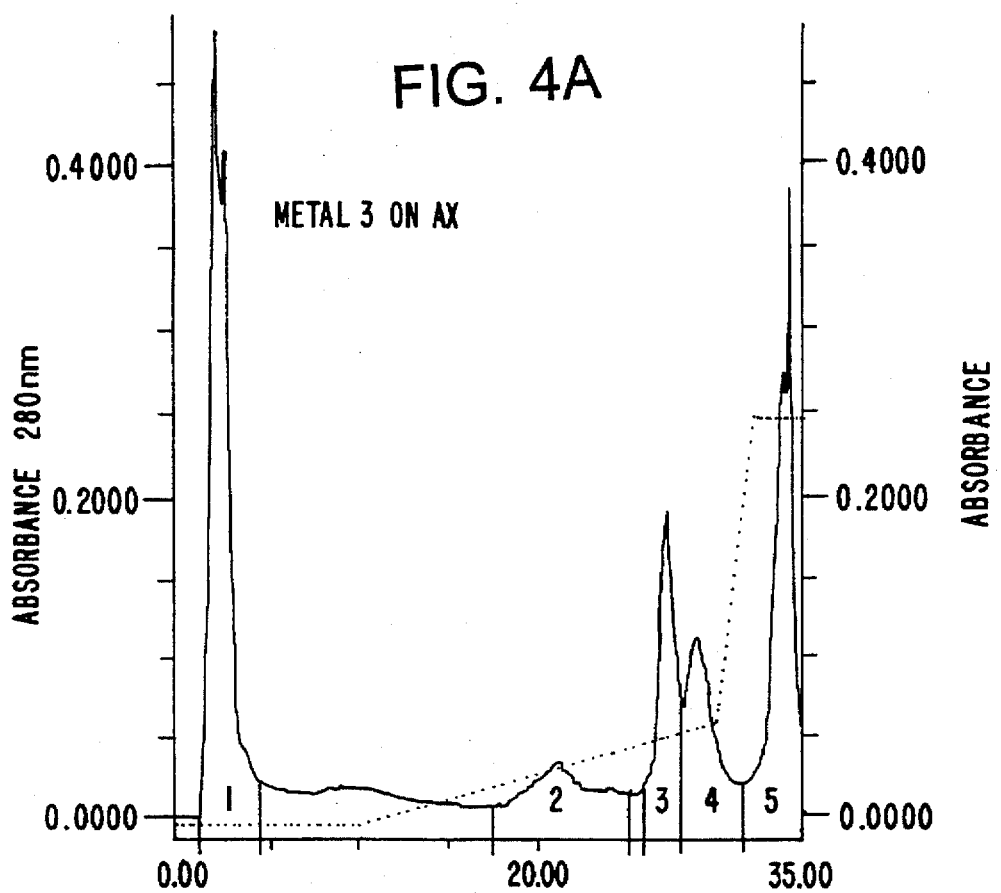
Figures 4B, 4D:
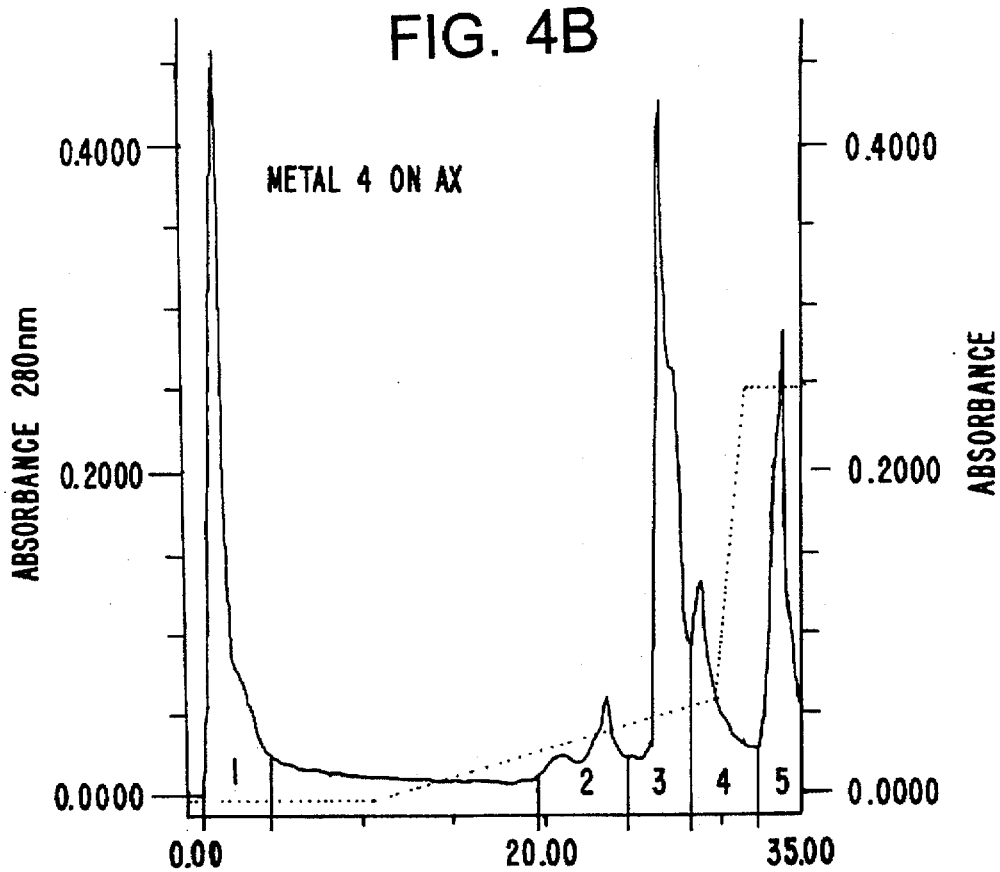

FIG. 4: Anion exchange chromatography of Metal 3 (FIG. 4A) and Metal 4 (FIG. 4B) fractions (FIG. 3) from IMAC of *Filistata hibernalis* whole venom and bioassay (FIGS. 4C and 4D) in TBW of combined, like fractions from two AX chromatographies.

FIG. 5: Anion exchange chromatography of FIL-376 sample (AX 3 from FIG. 4).

Figures 6A, 6B:
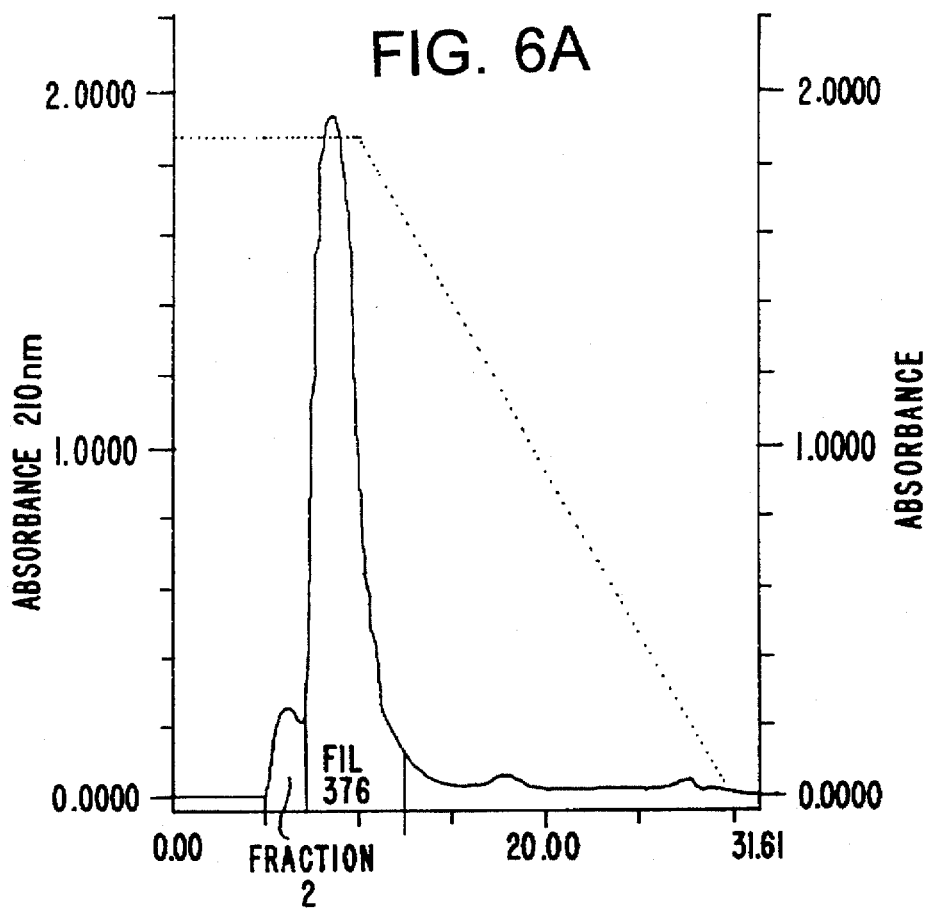

FIG. 6: Hydrophobic interaction chromatography (FIG. 6A) of FIL-376 fraction from anion exchange chromatography shown in FIG. 5 and bioassay (FIG. 6B) of the fractions in TBW.

Figures 7A, 7B:
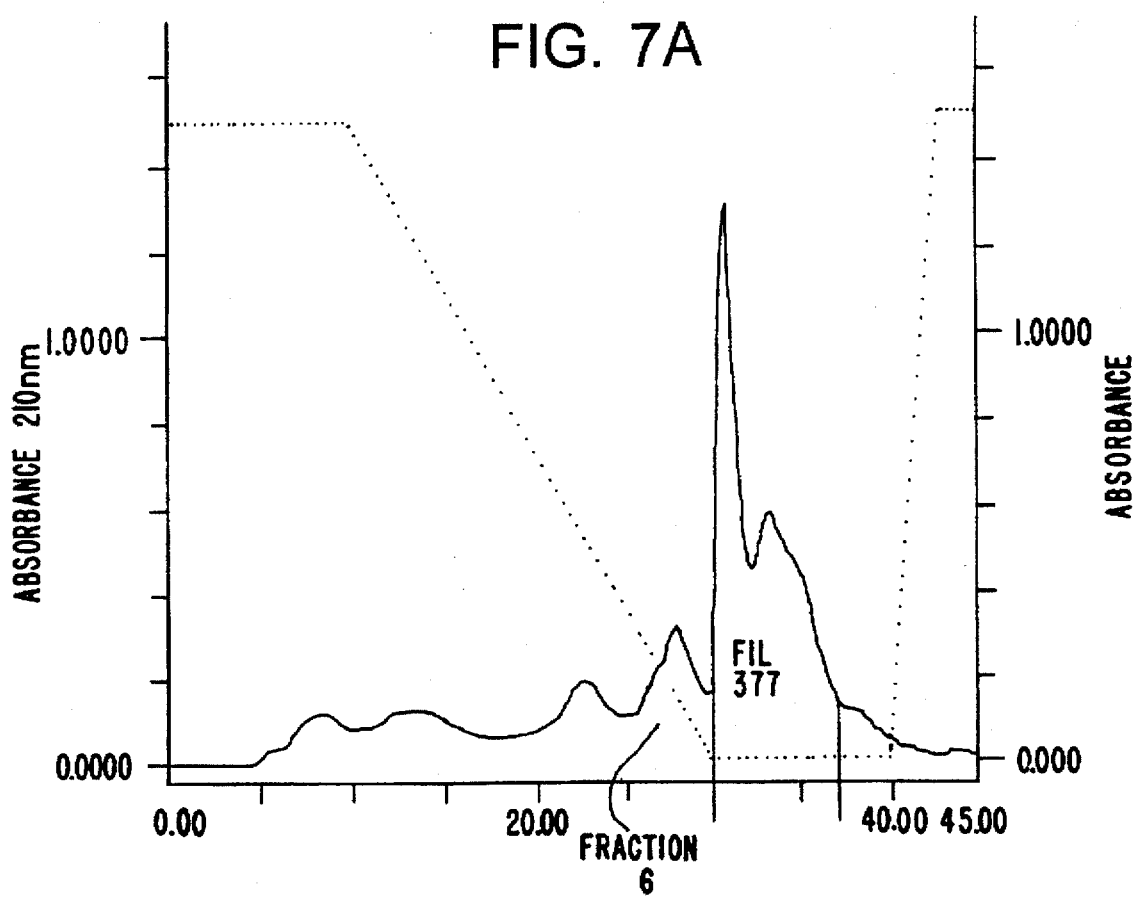

FIG. 7: Hydrophobic interaction chromatography (FIG. 7A) of the FIL-377-containing fraction (AX1) from the anion exchange chromatography shown in FIG. 4 and bioassay (FIG. 7B) results in TBW.

FIG. 8: A second anion exchange chromatography of the FIL-502-containing fraction (AX3) from the anion exchange chromatography shown in FIG. 4.

Figures 9A, 9B:
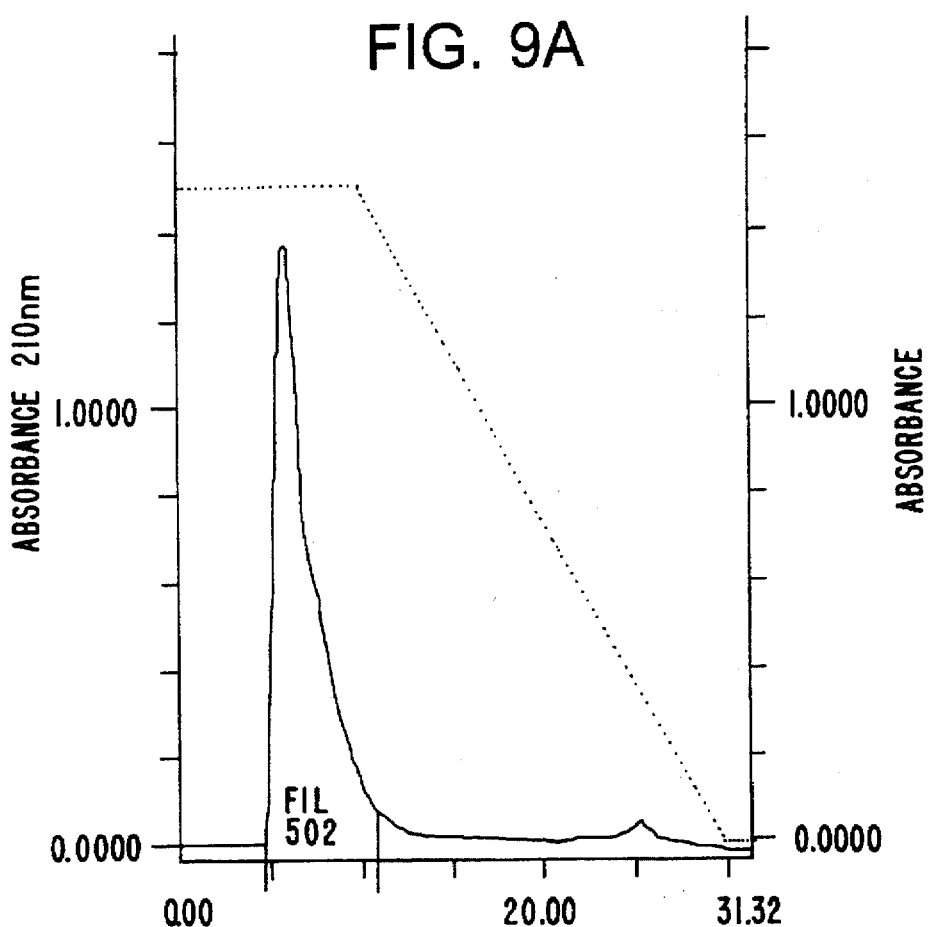

FIG. 9: Hydrophobic interaction chromatography (FIG. 7A) of FIL-502 from the anion exchange chromatography shown in FIG. 8 and bioassay (FIG. 9B) of the sample in TBW.

Figures 10A, 10B:
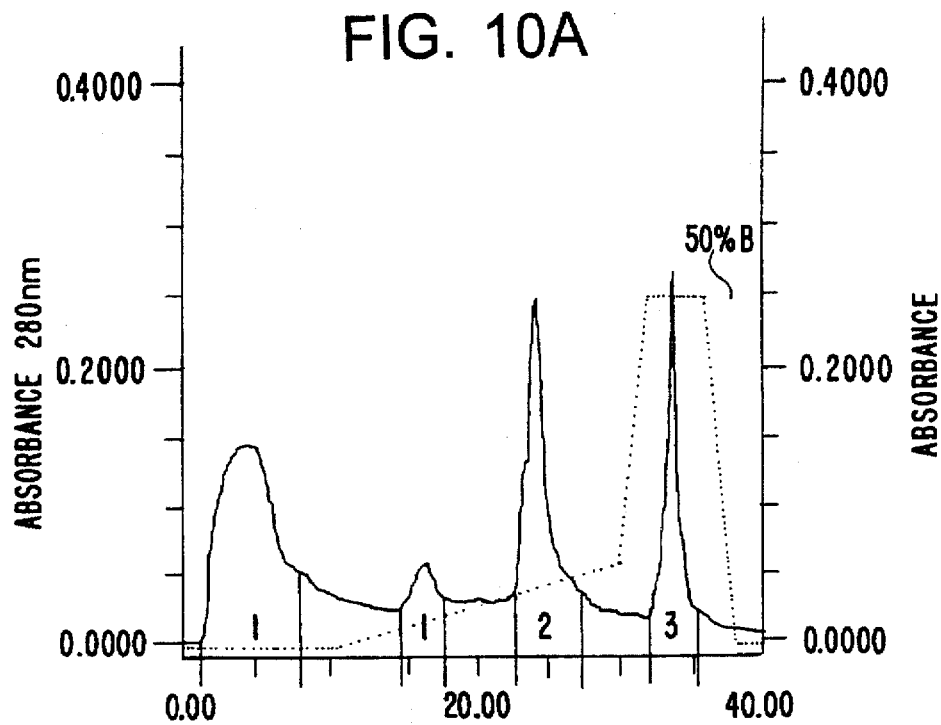

FIG. 10: Anion exchange chromatography (FIG. 10A) of the FIL-501-containing fraction (Metal 2) from the IMAC fractionation shown in FIG. 2 and bioassay (FIG. 10B) results in TBW.

Figures 11A, 11B:
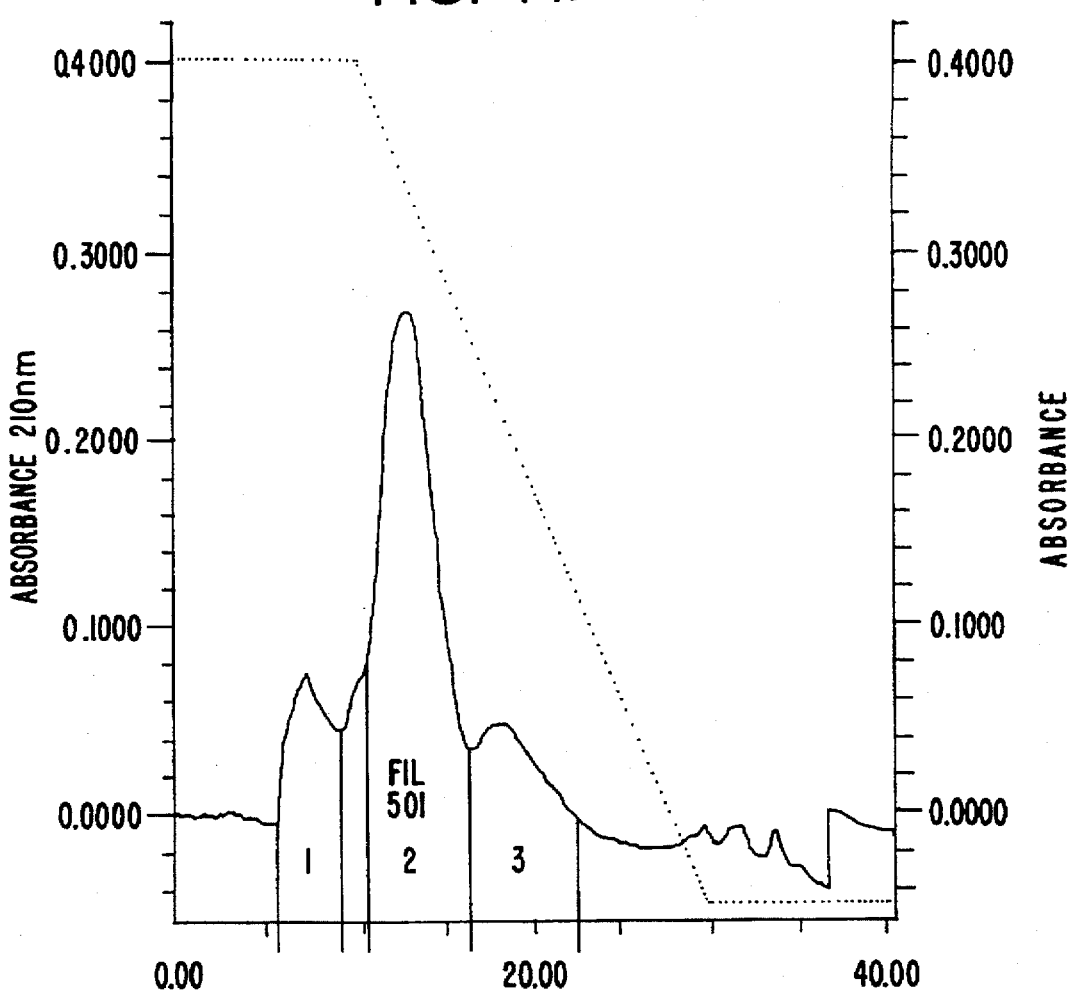

FIG. 11: Hydrophobic interaction chromatography (FIG. 11A) of the FIL-501-containing fraction (AX2) from the chromatography shown in FIG. 10 and bioassay (FIG. 11B) of the fractions in TBW.

Figure 12:
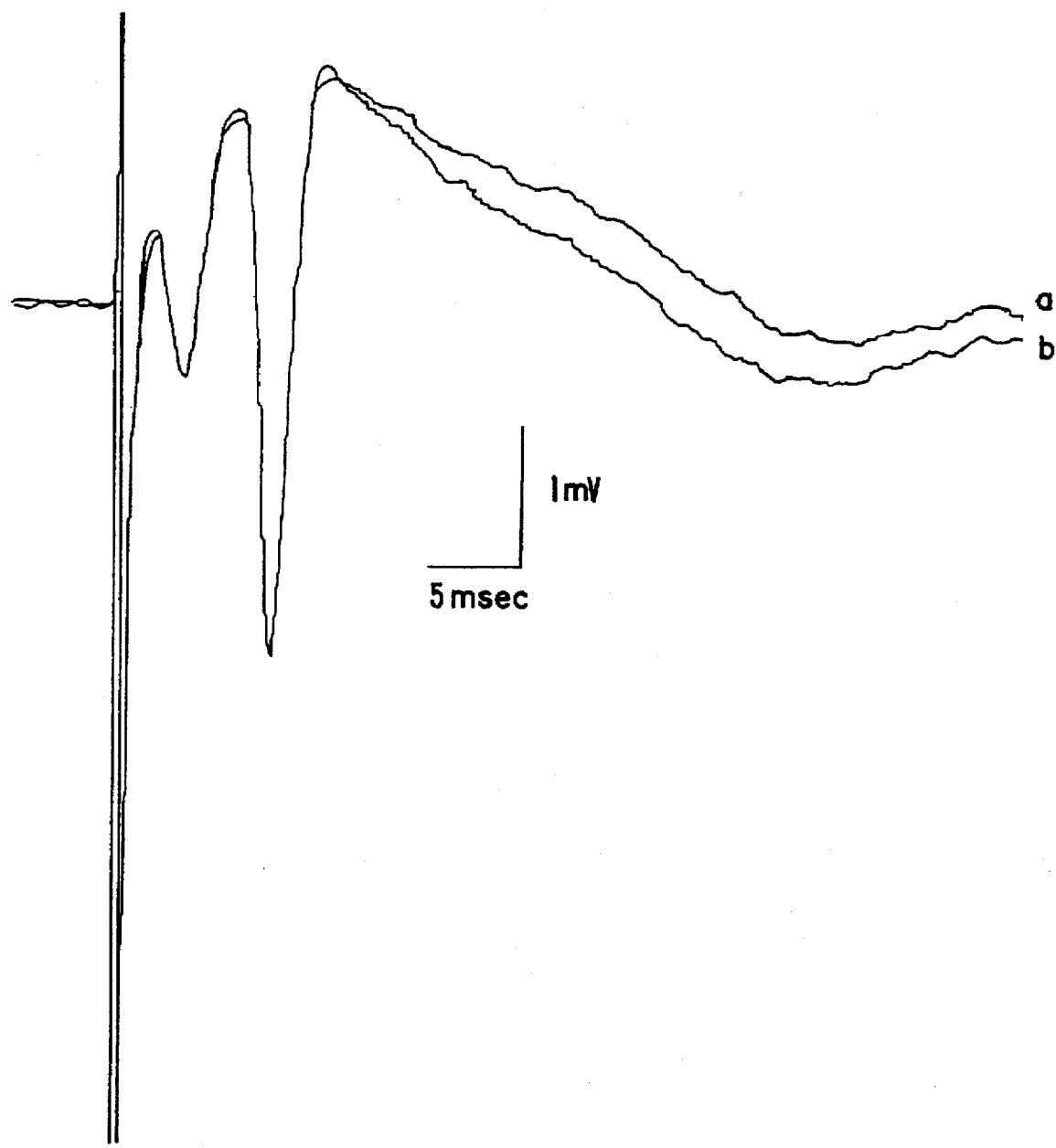

FIG. 12: The effect of FIL-377 on synaptic transmission (evoked population spike) at the Schaffer collateral-CA1 pyramidal cell synapse in rat hippocampal slices. These data represent the time-averaged population spike recordings (a) for 5 minutes prior to FIL-377 addition and (b) during the 15–20 minute interval following FIL-377 addition at 0.25 and 1 µM. These recordings are superimposable, indicating that, at these concentrations, FIL-377 has no activity in the rat CNS that can be detected in this assay.

DETAILED DESCRIPTION OF THE INVENTION

Spiders in the genus Filistata are members of the family Filistatidae. The genus Filistata is the most common in the family, and *Filistata hibernalis* is perhaps the most widely distributed species in the genus. *Filistata hibernalis* is a common house spider in the southern United States, spinning large, flat webs which are frequently seen on the outside walls of buildings. The spider generally hides in a crevice at the center of the web and waits for a disturbance of the web to indicate that prey has been captured.

The mechanism of action of the insecticidally effective proteins of this invention is unknown. It has been found that these toxins produce a unique set of symptoms in various species of insects. The toxins cause a distinctive, gradually developing flaccid paralysis. This is often accompanied by a characteristic discoloration, usually appearing first at the point of injection, which slowly spreads until the entire insect is severely discolored. These effects are identical to those caused by whole Filistata venom, strongly implying that the toxic proteins described in this invention are primarily responsible for the insecticidal effects of this venom.

A. The Isolation of proteins from Filistata venom

One source of insecticidally effective proteins is Filistata venom. Spider venom can be removed from Filistata by any method known such as venom gland extraction from cephalothorax. However, in order to avoid impurities within the spider venom and the isolated toxins, the spider venom preferably is obtained by electrical stimulation of the spiders to cause release of the venom and subsequent suction to collect the released venom and prevent contamination of the venom by regurgitate or hemolymph as described in U.S. Pat. No. 4,925,664.

Once the spider venom is obtained by electrical milking techniques, it can be fractionated into its protein (toxin) components by high performance liquid chromatography (HPLC) with a variety of separation modes such as hydrophobic interaction, ion exchange and immobilized metal ion affinity (IMAC) chromatography.

Thus, using the technique of electrically milking the spider coupled with HPLC using IMAC, hydrophobic interaction and ion exchange columns, it is possible to obtain substantially purified spider toxins. It will be appreciated, however, that other equivalent techniques may also be employed within the scope of the present invention in order to isolate the spider toxins. The toxins thus isolated can be assayed for insecticidal activity and the DNA and amino acid sequences determined by methods known to those in the art.

B. Insecticidally effective proteins

This invention, in one of its aspects, provides a family of insecticidally effective proteins, and insecticidally effective fragments thereof and agriculturally or horticulturally acceptable salts thereof.

Once an insecticidally effective, protein-containing fraction has been isolated from a source and purified as described herein, amino acid sequence determination can be performed in any way known to those in the art such as N-terminal amino acid sequencing and use of an automated amino acid sequencer.

It will be understood from this disclosure that additional insecticidally effective proteins are expected to be within the scope of the invention. That is, it is believed other insecticidally effective proteins in the family exist and may be isolatable from Filistata as well as other sources in addition to the four detailed herein. The following relates to a family of insecticidally effective proteins. Members of this family of insecticidally effective proteins are believed to share the following characteristics:

1) weight ranging between about 22,628 to 27,750 amu; and 2) a characteristic effect when injected into insects.

More specifically, FIL-376 has a mass of about 22,850.20±0.76 amu as determined by mass spectroscopy. A subclone, assigned the name FIL-705, was sequenced in its entirety using two flanking and internal primers. FIL-705 encodes a protein which is significantly larger than FIL-376 and it is speculated that this molecule may be a precursor for FIL-376 or otherwise a related molecule.

The DNA sequence of the cDNA contained in the subclone FIL-705 is presented in SEQ ID NO:1 and the amino acid sequence in SEQ ID NO:2. Encoded amino acid residues #6–40 are in direct agreement with N-terminal sequence analysis of FIL-376 (SEQ ID NO:3). The tentative assignments for residues #41–50 are 90% homologous to those encoded by the cDNA; a Leu residue is encoded at residue 43 rather than the Gly which was presented tentatively by amino acid sequencing. Comparison of several FIL-376 subclones suggest the following variations in amino acid sequence:

| Nucleic Acid Change | Amino Acid Change | Change in MW |
| --- | --- | --- |
| A —> G | Met —> Thr (#167) | −30 daltons |
| T —> A | Lys —> Asn (#195) | −14 daltons |

FIL-377 has a mass of about 27,704.05±0.85 amu as determined by mass spectroscopy. The N-terminal amino acid sequence of FIL-377 is presented in SEQ ID NO:4.

A third and fourth member of this family, FIL-501 and FIL-502, were also isolated. The N-terminal amino acid sequences of FIL-501 and FIL-502 are presented in SEQ ID NOS:5 and 6, respectively. FIL-501 has a mass of about 22,629.0±0.79 amu.

C. Identification of the coding sequence of insecticidally effective proteins of this invention A substantially isolated DNA sequence encoding a protein of this invention may be determined by methods known to those in the art.

Employing partial amino acid sequence data, the genes responsible for the production of proteins from a source can be isolated and identified. Numerous methods are available to obtain the gene responsible for the production of a protein. Examples include Fuqua, S. et al., "A simple PCR method for detection and cloning low abundant transcript", *Biotechnique*, Vol. 9, No. 2 (August 1990); Frohman, M. A., "RACE: Rapid amplification of cDNA ends", PCR protocols, ed. Innis et al., Academic Press, San Diego, Calif. (1990) and U.S. Pat. No. 4,703,008 "DNA Sequences Encoding Erythropoietin" which patent is incorporated by reference.

Briefly, a DNA molecule is synthesized which encodes the determined amino acid sequence or which represents the complementary DNA strand to such a DNA molecule which encodes the determined amino acid sequence. This synthetic DNA molecule may then be used to probe for DNA sequence homology in cell clones containing recombinant DNA molecules comprising, in part, DNA sequences derived from the genomic DNA of an organism such as a spider or derived from cDNA copies of mRNA molecules isolated from cells or tissues of an organism such as a spider. Generally, DNA molecules of fifteen (15) nucleotides or more are required for unique identification of an homologous DNA, said number requiring unique determination of at least five (5) amino acids in sequence. It will be appreciated that the number of different DNA molecules which can encode the determined amino acid sequence may be very large since each amino acid may be encoded for by up to six (6) unique trinucleotide DNA sequences or codons. Therefore, it is impractical to test all possible synthetic DNA probes individually, and pools of several such DNA molecules are used concomitantly as probes. The production of such pools which are referred to as "degenerate" probes is well known in the art. It will also be appreciated that while only one DNA molecule in the probe mixture will have an exact sequence homology to the gene of interest, several of the synthetic DNA molecules in the pool may be capable of uniquely identifying said gene since only a high degree of homology is required. Therefore, successful isolation of the gene of interest may be accomplished with synthetic DNA probe pools which do not contain all possible DNA probe sequences. In general, codons which are infrequently utilized by the organism need not be represented in the probe pool. In fact, a single sequence DNA probe may be produced by including only the DNA codons most frequently utilized by the organism for each amino acid, although, it will be appreciated that this approach is not always successful.

One technique to isolate a gene sequence employs the Polymerase Chain Reaction (PCR). See e.g., U.S. Pat. Nos. 4,683,195 and 4,683,202 which patents are incorporated by reference as if fully set forth herein. Essentially PCR allows the production of a selected DNA sequence when the two terminal portions of the sequence are known. Primers, or oligonucleotide probes, are obtained which correspond to each end of the sequence of interest. Using PCR, the central portion of the DNA sequence is then synthetically produced.

In one such method of employing PCR to obtain the gene which encodes a unique spider venom gene, RNA is isolated from the spider and purified. A deoxythymidylate-tailed oligonucleotide is then used as a primer in order to reverse transcribe the spider mRNA into cDNA. A synthetic DNA molecule or mixture of synthetic DNA molecules as in the degenerate probe described above is then prepared which can encode the amino-terminal amino acid sequence of the venom protein as previously determined. This DNA mixture is used together with the deoxythymidylate-tailed oligonucleotide to prime a PCR reaction. Because the synthetic DNA mixture used to prime the PCR reaction is specific to the desired mRNA sequence, only the desired cDNA will be effectively amplified. The resultant product represents an amplified cDNA which can be ligated to any of a number of known cloning vectors. Not withstanding this, it will be appreciated that "families" of proteins or peptides may exist in spider venoms which will have similar amino acid sequences and that in such cases, the use of mixed oligonucleotide primer sequences may result in the amplification of one or more of the related cDNAs encoding these related proteins. Genes encoding related proteins are also within the scope of the invention as the related proteins also have useful insecticidal activities.

Finally, the produced cDNA sequence can be cloned into an appropriate vector using conventional techniques, analyzed and the nucleotide base sequence determined. A direct amino acid translation of these PCR products will reveal that they corresponded to the complete coding sequence for the mature protein. The portion of the DNA sequence which might encode amino acids corresponding to precursor and or propeptide regions may not be obtained by this approach. Such sequences may be determined by isolation of genomic or cDNA clones using the cDNA clone produced in this approach as a hybridization probe which is within the scope of the art.

D. Application of the proteins as insecticides

The insecticidally effective proteins of this invention are believed to be useful in controlling invertebrate pests such as those in the order Lepidoptera. Methods for using the insecticidally effective proteins of this invention may include contacting the pests with an effective amount of a protein of this invention.

Methods of contacting an invertebrate pest with a protein to control said pests are known. Examples include the insertion of a gene encoding a toxic peptide or protein into the genome of a baculovirus, such as the *Autographa californica* nuclear polyhedrosis virus. Of course, methods of controlling invertebrate pests using the proteins of this invention can be used in combination with other methods of controlling pests.

E. Recombinant expression

As used herein, "expression vector" includes vectors which are capable of expressing DNA sequences contained therein, where such sequences are operably linked to other sequences capable of effecting their expression, i.e., promoter sequences. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition, and any DNA sequence which is capable of supporting expression of a specified DNA code disposed therein is included in this term as it is applied to the specified sequence. In general, expression vectors of utility in recombinant DNA techniques are often in the form of "plasmids" which refer to circular double stranded DNA which, in their vector form are not bound to the chromosome. "Plasmid" and "vector" are used interchangeably as the plasmid is the most commonly used form of vector. However, the invention is intended to include such other forms of expression vectors which serve equivalent functions and which become known in the art subsequently hereto.

"Recombinant host cells" refers to cells which have been transformed with vectors constructed using recombinant DNA techniques.

Further provided by this invention is a recombinant expression vector comprising a DNA sequence which encodes an insecticidally effective peptide substantially isolatable from Filistata spider venom. The vector is capable of effecting the expression of the coding sequence in transformed cells. Also provided by the invention are recombinant host cells with a DNA sequence encoding an insecticidally effective peptide substantially isolatable from Filistata spider venom in a manner allowing the host cell to express the peptide.

Such recombinant expression vectors may be employed in methods for producing insecticidally effective peptides. Such methods comprise culturing recombinant host cells wherein a recombinant expression vector transformed, transfected or otherwise applied in said host cells has a DNA sequence encoding the peptide and recovering the insecticidally effective peptide from the recombinant host cell culture or host organism. In such methods the vector is capable of supporting with host cell factors the expression of the coding sequence in the transformed cells.

Provision of a suitable DNA sequence encoding the desired protein permits the production of the protein using recombinant techniques now known in the art. The coding sequence can be obtained by retrieving a cDNA or genomic sequence from a native source of the protein or can be prepared synthetically using the accurate amino acid sequence determined from the nucleotide sequence of the gene. When the coding DNA is prepared synthetically, advantage can be taken of known codon preferences of the intended host.

Expression systems containing the requisite control sequences, such as promoters, and preferably enhancers and termination controls, are readily available and known in the art for a variety of hosts. See e.g., Sambrook et al., *Molecular Cloning a Laboratory Manual*, Second Ed. Cold Spring Harbor Press (1989).

Thus, the desired proteins can be prepared in both procaryotic and eucaryotic systems, resulting, in the case of many proteins, in a spectrum of processed forms.

The most commonly used procaryotic system remains *E. coli*, although other systems such as *B. subtilis* and Pseudomonas are also expected to be useful. Suitable control sequences for procaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in procaryotic hosts in this matter, the signal sequence is removed upon secretion.

A wide variety of eucaryotic hosts are also now available for production of recombinant foreign proteins. As in bacteria, eucaryotic hosts may be transformed with expression systems which produce the desired protein directly, but more commonly signal sequences are provided to effect the secretion of the protein. Eucaryotic systems have the additional advantage that they are able to splice introns which may occur in the messenger RNA encoding proteins of higher organisms. Eucaryotic systems also provide a variety of post-translational mechanisms which result in, for example, glycosylation, oxidation or derivatization of certain amino acid residues, conformational control, and so forth.

Commonly used eucaryotic systems include yeast, insect cells, mammalian cells, avian cells, and cells of higher plants. The list is not exhaustive. Suitable promoters are available which are compatible and operable for use in each of these host types as well as are termination sequences and enhancers, as e.g. the baculovirus polyhedrin promoter. As above, promoters can be either constitutive or inducible. For example, in mammalian systems, the MTII promoter can be induced by the addition of heavy metal ions.

The particulars for the construction of expression systems suitable for desired hosts are known to those in the art. For recombinant production of the protein, the DNA encoding it is suitably ligated into the expression system of choice, and the system is then transformed into the compatible host which is then cultured and maintained under conditions wherein expression of the foreign gene takes place. The insecticidally effective protein of this invention thus produced is recovered from the culture, either by lysing the cells or from the culture medium as appropriate and known to those in the art.

It is understood that minor modifications of primary amino acid sequence may result in proteins which have substantially equivalent or enhanced activity as compared to the peptides exemplified herein. These modifications may be deliberate, as through site directed mutagenesis, or may be accidental such as through mutations in hosts which produce the peptide of the invention, all these modifications are included so long as insecticidal activity is retained. A "mutation" in a protein alters its primary structure (relative to the commonly occurring or specifically described protein) due to changes in the nucleotide sequence of the DNA which encodes it. These mutations specifically include allelic variants. Mutational changes in the primary structure of a protein result from deletions, additions, or substitutions. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral and polar, or neutral and nonpolar and/or aromatic. It is generally preferred that encoded peptides differing from the native form contain substituted codons for amino acids which are from the same group as that of the amino acid replaced.

Thus, in general, the basic amino acids Lys, Arg, and His are interchangeable; the acidic amino acids Asp and Glu are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable.

While Pro is a nonpolar neutral amino acid, it represents difficulties because of its effects on conformation, and substitutions by or for Pro are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by codons for amino acids from different classes may also be useful.

Because recombinant materials for the proteins of the invention are provided, these proteins can be made by recombinant techniques as well as by automated amino acid synthesizers. Because of the variety of post-translational characteristics conferred by various host cells, various modifications for the naturally-occurring proteins will also be obtained. A "modified" protein differs from the unmodified protein as a result of post-translational events which change the glycosylation, amidation or lipidation pattern, or the primary, secondary, or tertiary structure of the protein and are of course included within the scope of the invention as claimed.

It should be further noted that if the proteins herein are made synthetically, substitution by amino acids which are not encoded by the gene may also be made. Alternative residues include, for example, the ω amino acids of the formula $H_2N(CH_2)_n COOH$ wherein n is 2-6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

F. Genetically engineered insecticidal microbes

The insecticidally effective peptide alone or in combination with another insect toxin is expected to be useful in potentiating or enhancing the toxicity of microbes such as baculoviruses and hybrid bacteria.

Several baculoviruses including those that infect *Heliothis virescens* (cotton bollworm), *Orgyia pseudotsugata* (Douglas fir tussock moth), *Lymantria dispar* (gypsy moth), *Autographa californica* (alfalfa looper), *Neodiprion sertifer* (European sawfly), and *Laspeyresia pomonella* (codling moth) have been registered in some countries and used as pesticides. Introduction of at least one insect-selective toxin into the genome is expected to significantly enhance the potency of such pesticides.

A recombinant expression vector expected to be particularly suitable for use in this invention is a baculovirus expression vector such as the type disclosed in U.S. Pat. No. 4,879,236, which patent is incorporated by reference as if fully set forth herein. See also Carbonell et al. "Synthesis of a gene coding for an insect-specific scorpion neurotoxin and attempts to express it using baculovirus vectors," *Gene*, 73: 409–418 (1988). The vector is expected to be useful in a system where a DNA sequence encoding an insecticidally effective peptide substantially isolatable from Filistata spider venom can be cloned into baculovirus such as *Autographa californica* (AcMNPV) expression vector as described in U.S. Pat. No. 4,879,236 and Miller et al., *Science*, 219, 715–721 (1983). The recombinant expression vector virus could then be applied to the plant or animal upon which the insect is a pest, and when the virus is ingested by the pest insect, the recombinant virus will invade the cells of the intestinal wall and begin replication. During replication, the gene for the insecticidally effective protein will be expressed, resulting in the disablement or death of the insect in a shorter period than if the insect had ingested the wild type AcMNPV virus.

A hybrid virus also expected to be useful is taught in European Patent Application 0 340 948. The hybrid virus expressing the DNA of this invention is expected to yield a virus having an altered insect host range. For example, fusion proteins could be expressed as a single polypeptide product of a hybrid gene consisting of DNA of this invention and a specific insect gut cell recognition protein to direct the expressed insecticidally effective peptide to the host insect target.

Various prokaryotic and eukaryotic microbes can be transformed to express a hybrid toxin gene encoding an insecticidally effective protein by the method taught in European Patent Application 0 325 400.

Hybrid bacterial cells, comprising a plasmid with the gene coding for the protein of this invention are expected to be useful in the method of this invention. Insects would be controlled by applying the hybrids to insects. See e.g., U.S. Pat. No. 4,797,279 which patent is incorporated by reference as if fully set forth herein.

Other examples of employing baculovirus that would be suitable for use in this invention are described in Tomalski et al., "Insect paralysis by baculovirus-mediated expression of a mite neurotoxin gene", *Nature*, 352: 82–85 (1991) and Stewart et al., "Construction of an improved baculovirus insecticide containing an insect-specific toxin gene", *Nature*, 352: 85–88 (1991); McCutchen, et al., "Development of a recombinant Baculovirus expressing an insect seective Neurotoxin: Potential for Pest Control," *Biotechnology*, 9: 848–851 (1991).

An insecticidal composition comprising an insecticidally effective amount of a protein according to this invention and agriculturally or horticulturally acceptable salts thereof in an agriculturally or horticulturally acceptable carrier therefor is also provided.

EXAMPLES

The following examples are given to illustrate particular compositions and methods within the scope of the present invention but they are not intended to limit the scope of the present invention.

MATERIALS AND METHODS

GENERAL METHODS

The spider venom is preferably obtained by electrical stimulation of the spiders to cause release of the venom and subsequent suction to collect the released venom and prevent contamination of the venom by regurgitate or hemolymph as described in U.S. Pat. No. 4,925,664.

Crude venom (stored at −80° C.) was thawed and mixed thoroughly with the starting solvent prior to chromatography. The venom was fractionated by high performance liquid chromatography (HPLC) incorporating Beckman System Gold 126 solvent delivery and 168 photodiode array detector modules. The following columns and conditions were used in the purifications. Immobilized metal ion affinity chromatography (IMAC) was performed on a Progel ™TSK Chelate 5PW column (7.5×75 mm, from Supelco) freshly loaded with $Cu^{+2}$ ions (40 mM $CuSO_4$ (aq)). The A buffer was 20 mM $NaH_2PO_4$, 1 mM imidazole, 0.5M NaCl adjusted to pH 7.0 with 10M NaOH. The B buffer was 20 mM $NaH_2PO_4$, 20 mM imidazole, 0.5M NaCl adjusted to pH 7.0 with 10M NaOH. The column was equilibrated in the A buffer and eluted at a flow rate of 1 ml/min with a 17 min linear gradient (begun 5 min after injection) from 0 to 43% B buffer, followed by a 3 min gradient from 43–100% B. After 5 min at 100% B the column was returned to 0% B over 2 min and equilibrated before the next injection was made. The effluent was monitored at 280 nm and fractions collected with a Gilson model 203 fraction collector.

Anion exchange chromatography was performed on a MF-PLUS™ HEMA-IEC BIO Q column (4.6×150 mm, 10μ particle size, from Alltech Associates). The A buffer was 25 mM Tris base adjusted to pH 7.5 with 6N HCl and the B buffer was 25 mM Tris base, 1.0M NaCl adjusted to pH 7.5 with 6N HCl. The column was eluted at a flow rate of 1 ml/min with a 20 min linear gradient (begun 10 min after sample injection) from 0 to 12% B buffer. The column was then taken to 50% B over 2 min, held at 50% B for 4 min, returned to 0% B over 2 min and allowed to equilibrate before the next injection. This chromatography was monitored at 280 nm and fractions collected with a Gilson model 203 fraction collector.

Hydrophobic interaction chromatography was performed on a WP HI-Propyl ($C_3$) column (4.6×250 mm from J. T. Baker). Buffer A was 50 mM $NaH_2PO_4$ adjusted to pH 7.0 with 10 mM NaOH and buffer B was 50 mM $NaH_2PO_4$, 2M NaCl adjusted to pH 7.0 with 10M NaOH. Unless otherwise noted, the column was eluted at 0.5 ml/min with a 20 min linear gradient (begun 10 min after sample injection) from 75% B to 0% B. After 10 min at 0% B the column was returned to 75% B over 3 min and allowed to equilibrate before the next injection. The column was monitored at 220 nm and fractions collected with a Gilson model 203 fraction collector.

Ultrafiltration of the Filistata crude venom in Centricon™ C-10 and C-30 microconcentrators (Amicon) indicated that the insecticidal activity remained in the retentate. Therefore, HPLC column fractions were generally concentrated in Centricon™ C-10 microconcentrators for assay in TBW larvae as follows. Column fractions were place in C-10 filters and centrifuged at ~4000×g for 70 min (this concentrated the samples to ~200 μl). Two ml of phosphate buffered saline, pH 6.5 (PBS; 136.7 mM NaCl, 2.6 mM KCl, 1.46 mM $KH_2PO_4$, 8.0 mM $Na_2HPO_4$) was then added to the concentrate and the samples again centrifuged to give a final volume of 150–200 μl. Fractions were assayed for insecticidal activity by injection into *Heliothis virescens* (TBW) larvae as follows. TBW, 3 individuals for each fraction, were injected with 20 μg of test protein per g of larval weight; insects in the control group (5 larvae) were injected with equal volumes of PBS. After treatment the larvae were held in individual Petri dishes with food and observed periodically for paralysis and other effects such as feeding inhibition. Protein concentrations were determined using the Pierce BCA assay reagents and methods unless otherwise noted. N-terminal sequence analysis was performed at the Biotechnology Center at Utah State University in Logan, Utah. Mass spectral analysis of the proteins was obtained from the Biotechnology Research Institute in Montreal, Quebec, Canada.

Example 1

Initial Fractionation of Filistata hibernalis Whole Venom and Identification of Insecticidal Fractions from IMAC and Anion Exchange Chromatography Eight μl of whole venom was dissolved in 100 μl of A buffer (20 mM $NaH_2PO_4$, 0.5M NaCl, 1 mM imidazole adjusted to pH 7.0 with 10M NaOH) and loaded onto the TSK Chelate 5 PW column in the $Cu^{+2}$ form. The column was eluted at 1 ml/min with a 40 min linear gradient from 0% B to 100% B. Buffer B was 20 mM $NaH_2PO_4$, 0.5M NaCl, 20 mM imidazole adjusted to pH 7.0 with 10M NaOH. The column was monitored at 280 nm and fractions collected. The fractions were combined into 3 pools (FIG. 1) and concentrated in C-10 filters for testing in TBW as outlined in Methods. Only pool 2 showed appreciable insecticidal activity.

Fifty μl of whole venom was combined with 450 μl of A buffer (25 mM Tris base adjusted to pH 7.5 with 6M HCl) and loaded onto the HEMA-IEC BIO Q column equilibrated in the A buffer. The column was eluted at 1 ml/min with a 50 min linear gradient from 0 to 50% B (25 mM Tris base, 1M NaCl, adjusted to pH 7.5 with 6M HCl); the gradient was started 10 min after injection of the sample. The column was then taken to 100% B over 2 min, returned to 0% B over 4 min and allowed to equilibrate for the next run. The fractions were combined into 5 pools and concentrated in C-10 filters for testing in TBW as outlined in Methods (see FIG. 2). Pools 1–3 showed appreciable insecticidal activity.

Preliminary small scale chromatography on the HI-Propyl hydrophobic interaction column indicated that this column might be useful to separate the toxin components. Therefore, a larger scale isolation using IMAC, anion exchange and hydrophobic interaction chromatography was begun.

Example 2

Separation of 4 Insecticidal Components from 400 μl of Filistata hibernalis Whole Venom Four hundred μl of whole venom was chromatographed (in 80 μl aliquots) on the $Cu^{+2}$ loaded TSK Chelate 5PW (IMAC) column. Eighty μl portions of venom were added to 420 μl of A buffer and loaded onto the column which was eluted as described in Methods. Like fractions from all 5 runs were combined as shown in FIG. 3. Each pool was concentrated in a C-10 filter to a volume of ~300 μl. Pools were exchanged into PBS and pools 1, 2, and 5 reconcentrated to ~1 ml for testing in TBW. Pool 2 was saved for subsequent fractionation to give FIL-501. The majority of the insecticidal activity was expected to be in pools 3 and 4 (see Example 1), so these were concentrated to ~200 μl and chromatographed on the anion exchange column. Pool 3 was diluted to 1 ml with 25 mM Tris, pH 7.5, and chromatographed on the HEMA-BIO Q anion exchange column as described in Methods. Fractions were combined to give 5 pools as noted in FIG. 4.

Pool 4 from the IMAC column was also diluted to 1 ml with 25 mM Tris, pH 7.5, and chromatographed on the HEMA-BIO Q anion exchange column as described in Methods (see FIG. 4). Fractions were combined with like fractions from the anion exchange chromatography of IMAC Pool 3 described above to give samples AX 1–5.

Samples AX 1 through AX 5 were then concentrated in C-10 filters, exchanged into PBS and reconcentrated to ~500 μl for testing in TBW. All 5 pools showed some insecticidal activity. Pools 1, 3 and 4 contained the bulk of the protein and were fractionated further to give FIL-377, FIL-376 and FIL-502, respectively. Pools AX 3 and 4 were initially rechromatographed on the anion exchange column to try and improve the separation. Each was then subjected to hydrophobic interaction chromatography as a final purification step.

Example 3

Purification of FIL-376

Sample AX 3 from Example 2 was exchanged into 25 mM Tris, pH 7.5, in a C-10 filter and concentrated to a final volume of 1 ml. This sample was again chromatographed on the HEMA-IEC BIO Q column as described in Methods. The peak from this chromatography (FIG. 5) still appeared somewhat asymmetrical. Therefore, the material was chromatographed on a hydrophobic interaction column to see if it could be further purified. The column fractions were pooled as indicated in FIG. 5, concentrated in a C-10 filter, exchanged into PBS and reconcentrated to ~500 µl.

This 500 µl sample was adjusted to 1.5M in NaCl by addition of NaCl$_{(s)}$ and chromatographed on the HI-Propyl hydrophobic interaction column as described in Methods. FIL-376 is only slightly retained (FIG. 6), however, it was separated from a small impurity peak. The sample was concentrated in a C-10 filter and exchanged into PBS for assay in TBW as described in Methods.

A sample of FIL-376 prepared by a similar route was desalted by ultrafiltration versus water in a C-10 filter. The sample was divided into two portions and sent for N-terminal sequence and mass spectral analysis. The N-terminal sequence was found to be:

Ser-Asn-Asp-Glu-Pro-Leu-Tyr-Met-Glu-Ile-Val-Val-Ile-Xaa-Asp-Asn-Asn-Met-Phe-Lys-Lys-Tyr-Lys-Gly-Xaa-Val-Thr-Phe-Ile-Lys-Asp-Arg-Val-Gly-Ala-Ile-Ile-Asn-Gly-Ala . . . (SEQ ID NO:3) The mass was determined to be 22,850.20±0.76 amu. A typical yield of FIL-376 is 200–300 µg per ml of Filistata venom fractionated. E(1 mg/ml; 1 cm) at 280 nm is 1.0.

Example 4

Purification of FIL-377

FIL-377 was purified from pool AX 1 described in Example 2 above. The sample, 500 µl, was diluted to 2 ml with 50 mM NaH$_2$PO$_4$, 2M NaCl, adjusted to pH 7.0 with 10M NaOH. (Final NaCl concentration in the diluted sample was 1.5M.) This was chromatographed in 2×1 ml portions on the HI-Propyl hydrophobic interaction column as described in Methods (see FIG. 7). Like fractions from both runs were combined as indicated and concentrated in C-10 filters. The concentrates were exchanged into PBS and reconcentrated to ~400 µl for assay in TBW. This insecticidal component consistently elutes from the HI-Propyl column as two unresolved peaks but appears homogeneous by mass spectral, N-terminal and SDS-PAGE analysis.

A sample of FIL-377 prepared in a similar fashion was desalted on a Dynamax 300 Å C$_4$ column (4.6×250 mm) eluting with a 30 minute linear gradient from 5 to 60% B. Solvent A was 0.1% TFA (aq) and solvent B was 0.1% TFA in acetonitrile: FIL-377 elutes at ~50%B. The lyophilized, desalted sample was submitted for mass spectral and N-terminal sequence analysis. The N-terminal sequence was found to be:

Leu-Glu-Asp-Pro-Tyr-Lys-Ser-Asp-Ser-Asn-Ser-Arg-Tyr-Ile-Glu-Val-Val-Val-Val-Asn-Asp-Asn-Ser-Met-Phe-Arg-Lys-Tyr-Asn-Arg . . . (SEQ ID NO:4). The mass of FIL-377 was determined to be 27,704.05±0.85 amu. A typical yield of FIL-377 is ~1 mg per ml of Filistata venom fractionated. E (1 mg/ml; 1 cm) at 280 nm =1.0.

Example 5

Purification of FIL-502

Pool AX 4 from Example 2 was rechromatographed on the HEMA-BIO Q anion exchange column since it was poorly resolved from AX3 on the initial chromatography (see FIG. 4). The sample (400 µl) was exchanged into 25 mM Tris, pH 7.5, in a C-10 filter and concentrated to a final volume of ~1 ml. This was loaded onto the ion exchange column and eluted as described in Methods (FIG. 8). The fractions were pooled as noted on the chromatogram. The pool containing FIL-502 was then adjusted to 1.5M NaCl by addition of NaCl$_{(s)}$ and chromatographed on the HI-Propyl hydrophobic interaction column as described in Methods (see FIG. 9). This column did not affect any further purification since FIL-502 was not retained. Although the FIL-502 peak was somewhat asymmetrical, the sample was homogeneous by SDS PAGE and gave only one N-terminal sequence. The material was pooled as indicated, concentrated in a C-10 filter, exchanged into PBS and reconcentrated to ~300 µl for testing in TBW.

A small sample was desalted by ultrafiltration versus water in a C-10 filter and submitted for mass spectral and N-terminal sequence analysis. The N-terminal sequence was found to be:

Ser-Asp-Glu-Glu-Ser-Val-Xaa-Glu-Thr-Glu-Ile-Xaa-Lys-Glu-Xaa-Ala-Ile-Xaa-Leu-Xaa-Asn . . . (SEQ ID NO:6) Mass spectral analysis of FIL-502 was unsuccessful; no molecular ion was found.

Example 6

Purification of FIL-501

The Metal 2 fraction from FIG. 3 also showed insecticidal activity and was therefore subjected to anion exchange chromatography. One half of Metal 2 (~500 µl) was diluted to 5 ml with 25 mM Tris, pH 7.5, and chromatographed on the HEMA-BIO Q anion exchange column as described in Methods (FIG. 10). The fractions were pooled as indicated, concentrated in C-10 filters, exchanged into PBS, pH 6.5, and reconcentrated to ~350 µl for assay in TBW. Pool 2 was then subjected to hydrophobic interaction chromatography. A trial chromatography eluting the HI Propyl column under standard conditions (with a starting concentration of 1.5M NaCl) indicated that the compound was not well retained at that salt concentration. Therefore, the column was equilibrated in 100% B buffer (2M NaCl starting concentration) and pool 2 was adjusted to 2M NaCl by addition of NaCl$_{(s)}$. The sample was loaded onto the column and eluted with a 20 minute linear gradient begun 10 minutes after the sample was injected (0.5 ml/min flow rate) from 100 to 0% B buffer. (Buffers used for hydrophobic interaction chromatography are described in Methods.) The fractions were pooled as indicated in FIG. 11 and concentrated in C-10 filters. The pools were exchanged into PBS and concentrated to a final volume of ~200 µl for testing in TBW.

A small sample was desalted by ultrafiltration in a C-10 filter versus water. Samples were then sent for mass spectral and N-terminal sequence analysis. The N-terminal sequence was found to be:

Gly-Gly-Ser-Asp-Pro-Glu-Tyr-Met-Glu-Leu-Val-Val-Ile-Asn-Asp-Asn-Lys-Met-Phe-Arg-Lys-Tyr-Gly-Ser-Xaa-Thr-Xaa-Xaa-Val-Ala-Glu-Xaa-Xaa-Xaa-Gln-Xaa-Met-Asn-Ile-Ala . . . (SEQ ID NO:5) The mass of FIL-501 was found to be 22,629.0±0.79 amu.

Example 7

Isolating the coding genes for insecticidally effective peptides isolated from *Filistata hibernalis* venom Step #1: RNA Isolation Spiders are collected from external sources and identified as *Filistata hibernalis*. Live spiders are frozen and the cephalothorax removed under liquid nitrogen. RNA is extracted from the cephalothoraxes using the protocol of Chomczynski and Sacchi, *Analytical Biochemistry*, 162, 156 (1987). Polyadenylated messenger RNA (mRNA) is purified using oligo d(T) cellulose (Pharmacia LKB, Sweden) chromatography.

Step #2: cDNA Synthesis

Messenger RNA is reverse transcribed to cDNA with murine leukemia virus reverse transcriptase (Bethesda Research Laboratories, Md.) using the manufacturer's protocol. The 20 µl reaction mixture contains the enzyme buffer as supplied in a cDNA synthesis kit (Boehringer Mannheim, Ind.), 50 ng of mRNA, 2 units of RNase H, 30 ng of d(T)Not I primer (Promega, Madison, Wis.), 1 mM each deoxynucleoside triphosphates, and 100 µg of reverse transcriptase. The reaction mixture is incubated for 1 h at 37° C. and continued for 10 minutes at 42° C. The reaction mixture is ethanol precipitated and resuspended in 20 µl water.

Step #3: Primer Synthesis

A degenerate primer DNA sequence mixture which could code for amino acid residues 2 through 8 of Fil-376 is designed using codon preferences to reduce degeneracy.

Step #4: Amplification

Primer directed enzymatic amplification of DNA with a thermostable DNA polymerase was initially described by Saikki et al., *Science*, 239: 487 (1988). For this application, 5 µl of the Filistata cephalothorax cDNA is used as template in a polymerase chain reaction containing reagents contained in the GeneAmp™ DNA amplification kit (Perkin Elmer Cetus, Calif.). The amplification reaction contains the sense and antisense primers in a 2 µM concentration, 100 µM of each deoxynucleotide triphosphate, and 4 units of the thermostable recombinant Taq I polymerase. The reaction is run in a DNA Thermal Cycler manufactured by Perkin Elmer Cetus using both high and low stringency reactions.

Step #5: Cloning of PCR Products

The gel-purified PCR products are separated from unincorporated primers using a Centricon-100 (Amicon) molecular size separation unit. The retained products are then digested with the restriction enzyme Not I (MBR), Milwaukee, Wis.), which cleaves within the downstream (3' end) primer leaving a sticky end. The vector, pKS (Stratagene, LaJolla, Calif.), is double digested with EcoR V (US Biochemical) and Not I to generate sites specific for directional cloning. Vector and insert are ligated and transformed into compex DH5αF'. Colony lifts are screened with the $^{32}$P labeled internal probe and candidate colonies are further characterized by sequencing (US Biochemical's Sequenase Version 2.0) mini-prep DNA using the internal probe as primer.

Example 8

Recombinant Baculovirus Construction

A lepidopteran signal sequence (Jones et al., Molecular Cloning Regulation and Complete Sequence of a Hemocyanin-Related Juvenile Hormone-Suppressible Protein From Insect Hemolymphs, *J. Biol. Chem.* 265: 8596 (1990)), is constructed from two synthetic oligonucleotides using the method of Rossi, et al. (*J. Biol. Chem.* 257: 9226 (1982)). Two 48mers are purified by ion exchange chromatography. These two oligonucleotides share eleven base pairs of complementary sequence at their 3' termini. When the sequences are annealed in the presence of the four deoxy-ribonucleoside triphosphates and the Klenow fragment of DNA polymerase I, a double-stranded product is synthesized. Reaction products are purified using hydroxylapatite chromatography and the double-stranded DNA molecules are digested with the restriction enzymes appropriate for inserting this sequence upstream of the cDNA encoding FIL-705. Subclones are screened for the insertion of the signal sequence and evaluated by DNA sequencing.

DNA sequencing confirms an in-frame fusion between the two cDNA sequences. The entire synthetic gene construct is excised and adapted for cloning into the NheI site of pBlueBac, a baculovirus transfer vector [Vialard, J., et al., *J. Virology* 64: 3-50 (1990)]. Subclones are sequenced to confirm the correct insertion of the construct. The use of the pBlueBac vector expedites the screening process as insertion of the recombinant gene into the baculovirus genome is accompanied by co-expression of β-galactodidase and detectable by a color change when grown on indicating media.

Recombinant baculoviruses are produced by transfection of Spodoptera frugiperda strain Sf9 (ATCC#CRL1711) cells with a mixture of 1 µg AcMNPV viral DNA and 2 µg plasmid DNA using the protocol of Summers and Smith (in "A Manual of Methods for Baculovirus Vectors and Insect Cell Culture Procedures", Texas Agricultural Experiment Bulletin No. 1555, 1988). Four days post-transfection, dilutions of the cell supernatant are plaqued on 100 mm plates seeded with $5 \times 10^6$ Sf9 cells and covered with agarose containing Bluo-gal (Gibso BRL, Gaithersburg, Md.) as substrate. Within 5 to 6 days, recombinants are detectable by their pale blue color. Plaques are picked using a pasteur piper and eluted in 1 ml of media. This eluent is used to re-infect Sf9 cells seeded into a T-25 flask. Three days post-infection a small volume of supernatant is collected from six different isolates and used to prepare viral DNA. PCR amplification using viral specific primers from the region surrounding the polyhedrin gene confirms that viral isolates contain an appropriately sized insert and lacked any wild-type contamination. Tittered stocks of the recombinant viruses are then prepared for in vivo and in vitro testing.

BIOLOGICAL ACTIVITY DATA

INSECTICIDAL ACTIVITY

The insects tested were last instar, laboratory reared larvae of the tobacco budworm, *Heliothis virescens* (TBW); the beet armyworm, *Spodoptera exigua* (BAW); and the cabbage looper, *Trichoplusia ni* (CL). All three species are in the family Noctuidae of the order Lepidoptera. All samples, whether whole venom or venom fractions, were prepared in filter-sterilized physiological saline (PBS), pH 6.5. Samples were administered by injection into the hemocoel at or near the lateral midline of the fourth abdominal segment; the needle was inserted at a shallow angle to avoid injury to internal organs. Whole venom doses were calculated in terms of whole venom equivalents (WVE). One WVE is the amount of any material which is normally present in one microliter of whole milked venom. Doses of components from early fractionations were also calculated in terms of WVE. Doses of purified toxins were calculated by protein assay, or by measuring short wavelength ultraviolet absorbances (Scopes, *Anal. Biochem.* 59: 277 (1974); Waddell, *J. Lab. Clin. Med.* 48: 311 (1956)). Both methods gave similar results, with calculated concentrations varying by a factor of less than 2.

Dose-response tests by injection in TBW (n=8) indicate that FIL-376 and FIL-377 have quite similar insecticidal activities (table 1). $LD_{50}$ values were determined by probit analysis (M. Raymond, Ser. Ent. med et Parasitol. 22(2) :117–121 (1985)). In TBW, the $LD_{50}$ of FIL-377 is 4.8 µg/g (0.17 nmol/g), while the $LD_{50}$ of FIL-376 is 3.6 µg/g (0.16 nmol/g). In BAW, the $LD_{50}$ for FIL-376 is approximately 3.3 µg/g, while in CL this dose causes 75% mortality (table 2). Both FIL-376 and FIL-377 cause a slowly developing flaccid paralysis and the localized, gradually spreading necrotic discoloration which is characteristic of whole Filistata venom.

Further injection assays indicated that FIL-376 and FIL-377 are also insecticidally effective in larvae of the corn earworm (Heliothis virescens), fall armyworm (Spodoptera frugiperda), soybean looper (Pseudoplusia includens), European corn borer (Ostrinia nubilalis), and diamondback moth (Plutella xylostella). In these species, the estimated $LD_{50}$ of either FIL-376 or FIL-377 ranged from 1 to 10 µg/g (table 2). Thus, the overall pattern of susceptibility to Filistata toxins among these species is similar to that among TBW, BAW, and CL.

TABLE 1

Dose-response assays in tobacco budworm larvae with FIL-376 and FIL-377

| Toxin | Dose (µg/g) | % paralysis (48 hr) | % mortality (96 h) | n |
|---|---|---|---|---|
| FIL-376 | 30.0 | 87.5 | 87.5 | 8 |
|  | 15.0 | 100 | 100 | 8 |
|  | 7.50 | 75 | 75 | 8 |
|  | 3.8 | 50 | 50 | 8 |
|  | 1.9 | 25 | 25 | 8 |
| FIL-377 | 36.6 | 100 | 100 | 8 |
|  | 18.3 | 87.5 | 87.5 | 8 |
|  | 9.2 | 75 | 75 | 8 |
|  | 4.6 | 50 | 50 | 8 |
| Control | 0.0 | 0 | 0 | 8 |

| Toxin | $LD_{50}$ (µg/g) | 95% CI (lower) | 95% CI (upper) |
|---|---|---|---|
| FIL-376 | 3.60 | 1.80 | 5.65 |
| FIL-377 | 4.80 | 0.16 | 8.20 |

TABLE 2

Insecticidal activity of FIL-376 and FIL-377

| Species | Toxin | Dose (µg/g) | Assay Period | % paralysis | n | Eventual % mortality |
|---|---|---|---|---|---|---|
| Spodoptera exigua (beet armyworm) | FIL-376 | 10.0 | 48 hr | 65 | 20 | 65 |
|  |  | 3.3 | 48 hr | 50 | 20 | 50 |
|  |  | 0 (control) | 48 hr | 0 | 20 | 0 |
| Trichoplusia ni (cabbage looper) | FIL-376 | 10.0 | 48 hr | 85 | 20 | 85 |
|  |  | 3.3 | 48 hr | 75 | 20 | 75 |
|  | CONTROL | 0 | 48 hr | 0 | 20 | 0 |
| Spodoptera frugiperda (fall armyworm) | FIL-377 | 30.0 | 48 hr | 55 | 20 | 55 |
|  |  | 6.0 | 48 hr | 20 | 20 | 20 |
|  | CONTROL | 0 | 48 hr | 0 | 20 | 0 |
| Ostrinia nubilalis (European corn borer) | FIL-376 | 30.0 | 48 hr | 90 | 20 | 90 |
|  |  | 10.0 | 48 hr | 55 | 20 | 55 |
|  | CONTROL | 0 | 48 hr | 0 | 20 | 0 |
| Pseudoplusia includens (soybean looper) | FIL-376 | 6.0 | 48 hr | 50 | 4 | 50 |
|  |  | 1.5 | 48 hr | 0 | 4 | 0 |
|  | CONTROL | 0 | 48 hr | 0 | 4 | 0 |
| Plutella xylostella (diamondback moth) | FIL-376 | 10.0 | 24 hr | 100 | 10 | 100 |
|  |  | 3.3 | 24 hr | 100 | 10 | 100 |
|  |  | 1.1 | 24 hr | 100 | 10 | 100 |
|  | CONTROL | 0 | 24 hr | 10 | 10 | 100 |
| Heliothis zea (corn earworm) | FIL-376 | 20.0 | 48 hr | 83 | 6 | 83 |
|  |  | 5.0 | 48 hr | 100 | 6 | 100 |
|  | CONTROL | 0 | 48 hr | 0 | 6 | 0 |

MAMMALIAN TOXICOLOGY

FIL-376 and FIL-377 were tested in male Swiss-Webster mice (n=2) by intraperitoneal (i.p.) injection at a dose of 1 µg/g; neither protein had any visible effect up to 72 hours after injection, when observations were discontinued. These compounds were also tested several times in male Swiss-Webster mice (n≧4) by intracerebroventricular (i.c.v.) injection at doses from 0.2 to 0.67 µg/g; neither had any effect up to 72 hours p.i., when observations were discontinued.

FIL-377 was also assessed for its effect on synaptic transmission (evoked population spike) at the Schaffer collateral-CA1 pyramidal cell synapse in rat hippocampal slices. At 0.25 and 1 µM, it was without effect. The data depicted in FIG. 12 represent the time-averaged population spike recordings (a) for 5 minutes prior to FIL-377 addition and (b) during the 15–20 min interval following FIL-377 addition. These recordings are superimposable, indicating that, at these concentrations, FIL-377 has no activity in the rat CNS that can be detected in this assay. The assay is capable of detecting a variety of effects on various mammalian ion channels and neurotransmitter receptors (T.V. Dunwiddie, "The Use of In Vitro Brain Slices in Neuropharmacology". In Electrophysiological Techniques in Pharmacology (H. M. Geller, ed.), Alan R. Liss, Inc., New York (1986)).

TABLE 3

| Sequence ID # | Description |
|---|---|
| 1 | cDNA sequence encoding FIL-705 |
| 2 | Amino acid sequence of FIL-705 |
| 3 | N-terminal amino acid sequence of FIL-376 |
| 4 | N-terminal amino acid sequence of FIL-377 |
| 5 | N-terminal amino acid sequence of FIL-501 |
| 6 | N-terminal amino acid sequence of FIL-502 |

What is claimed:

1. A recombinant expression vector comprising a DNA sequence encoding an insecticidally effective protein from Filistata spider venom selected from the group consisting of:
    (a) a protein having a mass of about 22,850 amu and comprising an N-terminal amino acid sequence defined in SEQ ID NO:3;
    (b) a protein comprising an N-terminal amino acid sequence defined in SEQ ID NO:4;
    (c) a protein having a mass of about 22,625 amu and comprising an N-terminal amino acid sequence defined in SEQ ID NO:5; and
    (d) a protein comprising an N-terminal amino acid sequence defined in SEQ ID NO:6;
wherein said protein causes flaccid paralysis when injected into larvae of at least one member of the class Insecta, order Lepidoptera.

2. The recombinant expression vector according to claim 1 wherein said spider venom is from *Filistata hibernalis*.

3. The recombinant expression vector of claim 1, wherein said DNA sequence encodes a protein having a mass of about 22,850 amu and comprising an N-terminal amino acid sequence defined in SEQ ID NO:3.

4. The recombinant expression vector of claim 1, wherein said DNA sequence encodes a protein comprising an N-terminal amino acid sequence defined in SEQ ID NO:4.

5. The recombinant expression vector of claim 1, wherein said DNA sequence encodes a protein having a mass of about 22,625 amu and comprising an N-terminal amino acid sequence defined in SEQ ID NO:5.

6. The recombinant expression vector of claim 1, wherein said DNA sequence encodes a protein comprising an N-terminal amino acid sequence defined in SEQ ID NO:6.

7. A recombinant baculovirus expression vector comprising a DNA sequence encoding an insecticidally effective protein from Filistata spider venom selected from the group consisting of:
   (a) a protein having a mass of about 22,850 amu and comprising an N-terminal amino acid sequence defined in SEQ ID NO:3;
   (b) a protein comprising an N-terminal amino acid sequence defined in SEQ ID NO:4;
   (c) a protein having a mass of about 22,625 amu and comprising an N-terminal amino acid sequence defined in SEQ ID NO:5; and
   (d) a protein comprising an N-terminal amino acid sequence defined in SEQ ID NO:6;
   wherein said protein causes flaccid paralysis when injected into larvae of at least one member of the class Insecta, order Lepidoptera.

8. The recombinant baculovirus expression vector according to claim 7 wherein said spider venom is from *Filistata hibernalis*.

9. The recombinant baculovirus expression vector of claim 7, wherein said DNA sequence encodes a protein having a mass of about 22,850 amu and comprising an N-terminal amino acid sequence defined in SEQ ID NO:3.

10. The recombinant baculovirus expression vector of claim 7, wherein said DNA sequence encodes a protein comprising an N-terminal amino acid sequence defined in SEQ ID NO:4.

11. The recombinant baculovirus expression vector of claim 7, wherein said DNA sequence encodes a protein having a mass of about 22,625 amu and comprising an N-terminal amino acid sequence defined in SEQ ID NO:5.

12. The recombinant baculovirus expression vector of claim 7, wherein said DNA sequence encodes a protein comprising an N-terminal amino acid sequence defined in SEQ ID NO:6.

13. A recombinant host cell transformed or transfected of otherwise applied with a DNA sequence encoding an insecticidally effective protein from Filistata spider venom selected from the group consisting of:
   (a) a protein having a mass of about 22,850 amu and comprising an N-terminal amino acid sequence defined in SEQ ID NO:3;
   (b) a protein comprising an N-terminal amino acid sequence defined in SEQ ID NO:4;
   (c) a protein having a mass of about 22,625 amu and comprising an N-terminal amino acid sequence defined in SEQ ID NO:5; and
   (d) a protein comprising an N-terminal amino acid sequence defined in SEQ ID NO:6;
   wherein said protein causes flaccid paralysis when injected into larvae of at least one member of the class Insecta, order Lepidoptera.

14. A method for producing an insecticidally effective protein selected from the group consisting of:
   (a) a protein having a mass of about 22,850 amu and comprising an N-terminal amino acid sequence defined in SEQ ID NO:3;
   (b) a protein comprising an N-terminal amino acid sequence defined in SEQ ID NO:4;
   (c) a protein having a mass of about 22,625 amu and comprising an N-terminal amino acid sequence defined in SEQ ID NO:5; and
   (d) a protein comprising an N-terminal amino acid sequence defined in SEQ ID NO:6, which method comprises:
      (i) culturing recombinant host cells wherein a recombinant expression vector transformed or transfected or otherwise applied in said host cells comprises a DNA sequence encoding said protein, wherein the vector effects the expression of said coding sequence in host cells; and
      (ii) recovering said insecticidally effective protein from the recombinant host cell culture or host.

15. A method of controlling invertebrate pests comprising contacting said pests with a recombinant baculovirus expressing an insecticidally effective amount of a protein from Filistata spider venom selected from the group consisting of:
   (a) protein having a mass of about 22,850 amu and comprising an N-terminal amino acid sequence defined in SEQ ID NO:3;
   (b) a protein comprising an N-terminal amino acid sequence defined in SEQ ID NO:4;
   (c) a protein having a mass of about 22,625 amu and comprising an N-terminal amino acid sequence defined in SEQ ID NO:5; and
   (d) a protein comprising an N-terminal amino acid sequence defined in SEQ ID NO:6;
   wherein said protein causes flaccid paralysis when injected into larvae of at least one member of the class Insecta, order Lepidoptera.

16. The method of claim 15, wherein said protein has a mass of about 22,850 amu and comprises an N-terminal amino acid sequence defined in SEQ ID NO:3.

17. The method of claim 15, wherein said protein comprises an N-terminal amino acid sequence defined in SEQ ID NO:4.

18. The method of claim 15, wherein said protein has a mass of about 22,625 amu and comprises an N-terminal amino acid sequence defined in SEQ ID NO:5.

19. The method of claim 15, wherein said protein comprises an N-terminal amino acid sequence defined in SEQ ID NO:6.

* * * * *